United States Patent
Goldberg

(10) Patent No.: US 9,814,588 B2
(45) Date of Patent: Nov. 14, 2017

(54) GLENOID ARTHROPLASTY WITH MULTI-DIRECTIONAL FIXATION

(71) Applicant: CATALYST ORTHOSCIENCE INC., Naples, FL (US)

(72) Inventor: Steven S. Goldberg, Naples, FL (US)

(73) Assignee: CATALYST ORTHOSCIENCE INC., Naples, FL (US)

(*) Notice: Subject to any disclaimer, the term of this patent is extended or adjusted under 35 U.S.C. 154(b) by 0 days.

(21) Appl. No.: 15/228,443

(22) Filed: Aug. 4, 2016

(65) Prior Publication Data

US 2017/0042689 A1   Feb. 16, 2017

Related U.S. Application Data

(60) Provisional application No. 62/203,255, filed on Aug. 10, 2015.

(51) Int. Cl.
*A61F 2/40* (2006.01)

(52) U.S. Cl.
CPC .... *A61F 2/4081* (2013.01); *A61F 2220/0016* (2013.01)

(58) Field of Classification Search
CPC .... A61F 2/40; A61F 2/4081; A61F 2220/016; A61F 2/28; A61F 2/32
See application file for complete search history.

(56) References Cited

U.S. PATENT DOCUMENTS

| | | |
|---|---|---|
| 4,106,130 A | 8/1978 | Scales |
| 4,206,517 A | 6/1980 | Pappas |
| 4,550,450 A | 11/1985 | Kinnett |
| 4,865,605 A | 9/1989 | Dines |
| 4,964,865 A | 10/1990 | Burkhead |
| 4,986,833 A | 1/1991 | Worland |
| 5,030,219 A | 7/1991 | Matsen, III |
| 5,032,132 A | 7/1991 | Matsen, III |
| 5,383,936 A | 1/1995 | Kubein Meesenburg |
| 5,489,310 A | 2/1996 | Mikhail |
| 5,702,447 A | 12/1997 | Walch |
| 5,723,018 A | 3/1998 | Cyprien |
| 5,769,856 A | 6/1998 | Dong |
| 5,800,551 A * | 9/1998 | Williamson ....... A61B 17/1659 623/19.11 |
| 5,814,049 A | 9/1998 | Pratt |
| 5,919,195 A | 7/1999 | Wilson |
| 5,928,285 A | 7/1999 | Bigliani |
| 5,944,758 A | 8/1999 | Mansat |
| 5,976,144 A | 11/1999 | Fishbein |

(Continued)

FOREIGN PATENT DOCUMENTS

| AU | 2013209336 | 2/2014 |
|---|---|---|
| CA | 2821529 | 1/2014 |

(Continued)

*Primary Examiner* — Jason-Dennis Stewart
(74) *Attorney, Agent, or Firm* — Maywood IP Law; G. Jo Hays; David W. Meibos

(57) ABSTRACT

Arthroplasty components include an articular surface and a bone-facing surface. The bone-facing surface bears at least one anchoring element adapted for an oblique implantation trajectory. The anchoring element includes a reinforcement plate, a dowel, and surface features. Each surface feature resists forces acting along a different direction.

3 Claims, 14 Drawing Sheets

(56) References Cited

U.S. PATENT DOCUMENTS

| | | |
|---|---|---|
| 6,129,732 A | 10/2000 | Lechot |
| 6,245,074 B1 | 6/2001 | Allard |
| 6,364,910 B1 | 4/2002 | Shultz |
| 6,379,386 B1 | 4/2002 | Resch |
| 6,406,495 B1 | 6/2002 | Schoch |
| 6,475,221 B1 | 11/2002 | White |
| 6,673,115 B2 | 1/2004 | Resch |
| 6,679,916 B1 | 1/2004 | Frankle |
| 6,783,549 B1 | 8/2004 | Stone |
| 6,875,234 B2 | 4/2005 | Lipman |
| 6,911,047 B2 | 6/2005 | Rockwood, Jr. |
| 7,008,430 B2 | 3/2006 | Dong |
| 7,048,740 B2 | 5/2006 | White |
| 7,160,328 B2 | 1/2007 | Rockwood, Jr. |
| 7,204,854 B2 | 4/2007 | Guederian |
| 7,217,272 B2 | 5/2007 | Salyer |
| 7,294,149 B2 | 11/2007 | Hozack |
| 7,329,284 B2 | 2/2008 | Maroney |
| 7,588,572 B2 | 9/2009 | White |
| 7,621,962 B2 | 11/2009 | Lakin |
| 7,670,382 B2 | 3/2010 | Parrott |
| 7,780,669 B2 | 8/2010 | Lechot |
| 7,815,685 B2 | 10/2010 | Farrar |
| 7,867,234 B2 | 1/2011 | Collazo |
| 8,007,538 B2 | 8/2011 | Gunther |
| 8,038,719 B2 | 10/2011 | Gunther |
| 8,048,161 B2 | 11/2011 | Guederian |
| 8,080,063 B2 | 12/2011 | Ferrand |
| 8,157,866 B2 | 4/2012 | Winslow |
| 8,308,809 B2 | 11/2012 | Bishop |
| 8,425,614 B2 | 4/2013 | Winslow |
| 8,444,646 B2 | 5/2013 | Long |
| 8,465,548 B2 | 6/2013 | Long |
| 8,475,460 B1 | 7/2013 | Roger |
| 8,480,674 B1 | 7/2013 | Roger |
| 8,540,778 B2 | 9/2013 | Rhodes |
| 8,591,592 B2 | 11/2013 | Dreyfuss |
| 8,673,015 B2 | 3/2014 | Maroney |
| 8,764,836 B2 | 7/2014 | De Wilde |
| 8,778,028 B2 | 7/2014 | Gunther |
| 8,870,962 B2 | 10/2014 | Roche |
| 8,876,907 B2 | 11/2014 | Baptista |
| 8,974,537 B2 | 3/2015 | Dreyfuss |
| D730,522 S | 5/2015 | Goldberg |
| 9,119,643 B2 | 9/2015 | Winslow |
| 9,180,016 B2 | 11/2015 | Maroney |
| 9,233,003 B2 | 1/2016 | Roche |
| 9,237,894 B2 | 1/2016 | Hernandez |
| 9,283,076 B2 | 3/2016 | Sikora |
| 9,351,844 B2 | 5/2016 | Walch |
| D759,819 S | 6/2016 | Goldberg |
| 9,370,428 B2 | 6/2016 | Winslow |
| 9,433,507 B2 | 9/2016 | Reubelt |
| 9,474,619 B2 | 10/2016 | Reubelt |
| 9,610,166 B2 | 4/2017 | Gunther |
| 2003/0187449 A1 | 10/2003 | McCleary |
| 2003/0204263 A1 | 10/2003 | Justin |
| 2005/0049709 A1* | 3/2005 | Tornier .............. A61F 2/40 623/19.13 |
| 2005/0222572 A1 | 10/2005 | Chana |
| 2006/0074430 A1 | 4/2006 | Deffenbaugh |
| 2006/0094958 A1 | 5/2006 | Marquart |
| 2006/0111787 A1 | 5/2006 | Bailie |
| 2007/0055380 A1 | 3/2007 | Berelsman |
| 2007/0142917 A1 | 6/2007 | Roche |
| 2007/0219637 A1 | 9/2007 | Berelsman |
| 2007/0219638 A1 | 9/2007 | Jones |
| 2007/0244564 A1* | 10/2007 | Ferrand .............. A61F 2/4081 623/19.13 |
| 2008/0109000 A1 | 5/2008 | Maroney |
| 2008/0147070 A1 | 6/2008 | Michel |
| 2009/0192621 A1 | 7/2009 | Winslow |
| 2009/0226068 A1 | 9/2009 | Fitz |
| 2010/0087876 A1 | 4/2010 | Gunther |
| 2010/0087877 A1 | 4/2010 | Gunther |
| 2010/0161065 A1 | 6/2010 | Williams, Jr. |
| 2010/0228352 A1* | 9/2010 | Courtney, Jr. ........ A61F 2/4081 623/19.13 |
| 2010/0241235 A1* | 9/2010 | Basamania .......... A61F 2/4081 623/19.11 |
| 2010/0268239 A1 | 10/2010 | Sikora |
| 2011/0106266 A1 | 5/2011 | Schwyzer |
| 2011/0230972 A1 | 9/2011 | Katrana |
| 2012/0130500 A1 | 5/2012 | Maroney |
| 2012/0209392 A1 | 8/2012 | Angibaud |
| 2012/0310360 A1 | 12/2012 | Parrott |
| 2013/0024000 A1 | 1/2013 | Bojarski |
| 2013/0144393 A1 | 6/2013 | Mutchler |
| 2013/0166033 A1 | 6/2013 | Gunther |
| 2014/0257495 A1 | 9/2014 | Goldberg |
| 2015/0119891 A1 | 4/2015 | Goldberg |
| 2015/0320567 A1 | 11/2015 | Terrill |
| 2016/0089164 A1 | 3/2016 | Winslow |
| 2016/0095607 A1 | 4/2016 | Hernandez |
| 2016/0242921 A1 | 8/2016 | Walch |
| 2016/0287266 A1 | 10/2016 | Sikora |
| 2017/0014238 A1 | 1/2017 | Reubelt |

FOREIGN PATENT DOCUMENTS

| | | |
|---|---|---|
| CN | 101442961 | 11/2012 |
| CN | 102014800 | 4/2014 |
| CN | 105377195 | 3/2016 |
| DE | 10130796 | 1/2003 |
| DE | 10134511 | 2/2003 |
| EP | 1518519 | 3/2005 |
| EP | 1159939 | 7/2005 |
| EP | 2238949 | 10/2010 |
| EP | 2446859 | 5/2012 |
| EP | 2559406 | 2/2013 |
| EP | 2689751 | 1/2014 |
| EP | 2967892 | 1/2016 |
| FR | 2825263 | 12/2002 |
| FR | 2836821 | 5/2004 |
| GB | 2308068 | 9/1999 |
| WO | WO1998015241 | 4/1998 |
| WO | WO2000018335 | 4/2000 |
| WO | WO2002017822 | 3/2002 |
| WO | WO2006110896 | 10/2006 |
| WO | WO2007109800 | 9/2007 |
| WO | WO2009108591 | 9/2009 |
| WO | WO2012030794 | 3/2012 |
| WO | WO2013020026 | 2/2013 |
| WO | WO2014005644 | 1/2014 |
| WO | WO2014164265 | 10/2014 |
| WO | WO2015106136 | 7/2015 |

* cited by examiner

GLENOID ARTHROPLASTY WITH MULTI-DIRECTIONAL FIXATION

RELATED APPLICATIONS

The present application claims the benefit of:

U.S. Provisional Application No. 62/203,255, entitled GLENOID ARTHROPLASTY WITH MULTI-DIRECTIONAL FIXATION, which was filed on Aug. 10, 2015.

The foregoing is incorporated by reference as though set forth herein in its entirety.

TECHNICAL FIELD

The present disclosure relates to anchoring elements and articular surfaces for human or veterinary arthroplasty implants. The anchoring elements in this disclosure incorporate multi-directional fixation, also referred to as multi-directional resistance to pull-out. The disclosed anchoring elements are useful in situations where exposure is difficult, the implantation trajectory is oblique to the implantation site, or the implantation site is tapered, conical, or wedge-shaped. For example, the disclosed anchoring elements are useful in the context of a glenoid component for shoulder arthroplasty, so that the preparation of the glenoid and implantation of the glenoid component take place along an oblique surgical access and implantation trajectory. An oblique approach, or an antero-lateral approach, to the glenoid is technically simpler and less invasive than a lateral trajectory to the glenoid. This disclosure is made in the context of a glenoid component for shoulder arthroplasty for the purpose of illustrating the relevant principles of the technology. However, the principles disclosed herein are applicable to arthroplasty implants for other joints in human or animal skeletons, wherever an oblique implantation trajectory would simplify and reduce the invasiveness of the surgical technique.

In total shoulder arthroplasty, a glenoid implant is attached to a prepared glenoid or scapula, and a humeral implant is attached to a prepared humerus. The humeral implant usually includes a ball or convex articular surface at a proximal end thereof which engages and moves relative to a socket or concave articular surface formed in a lateral aspect of the glenoid implant, although this arrangement is sometimes reversed so that the humeral implant includes the convex articular surface and the glenoid implant includes the convex articular surface. The ligaments and muscles of the shoulder surround the implants and maintain the humeral implant against the glenoid implant, while at the same time allowing relative movement therebetween.

BACKGROUND

Some existing glenoid components include a fixation peg or a fixation keel on the medial bone-facing surface. Some designs include multiple parallel pegs. The peg or keel may include surface features to enhance fixation, such as alternating ridges and grooves, flanges, and the like. The surface features frequently extend perpendicular to the axis of the peg or keel, because the primary direction of pull-out occurs along that axis. Glenoid components may experience failure by pull-out along the peg or keel axis, but other failure modes occur as well. The humerus, or humeral component, contacts the glenoid component in multiple locations on the glenoid lateral articular surface in vivo. Thus, forces which may cause loosening occur in multiple locations and along multiple vectors.

Glenoid components may experience forceful loading applied to the peripheral edge of the implant, which may cause the opposite side of the component to lift up. Forceful loading of the far posterior peripheral edge is a known common failure mechanism of glenoid components. This failure mode may be referred to as lever-out failure or rotational pull-out.

Glenoid components may also experience side-to-side translation in the superior-inferior direction or in the antero-posterior direction. The most common direction is superior-inferior. Side-to-side translation is minimized when the implant peg, keel, or anchoring element is at least the same size as the bone tunnel into which it is inserted. However, the implant peg, keel, or anchoring element may be smaller than the bone tunnel, especially if the glenoid component will be fixed with bone cement. In this situation, the glenoid component is free to translate side-to-side, at least until the bone cement has hardened.

There is a need for an implant which resists axial pull-out, rotational pull-out (or lever-out), and translation.

The fundamental geometry of the anchoring elements disclosed herein provides inherent resistance to axial pull-out, rotational pull-out, and translation. The surface features disclosed herein are oriented in multiple planes to provide additional resistance to axial pull-out perpendicular to the back side of the glenoid component, pull-out along the axis of the dowel, and side-to-side translation in the superior-inferior or anterior-posterior directions.

SUMMARY

The various systems and methods of the present technology have been developed in response to the present state of the art, and in particular, in response to the problems and needs in the art that have not yet been fully solved by currently available arthroplasty implants. The systems and methods of the present technology may provide multi-directional resistance to pull-out and translation forces acting on the implants.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

DETAILED DESCRIPTION

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Figure 1A:
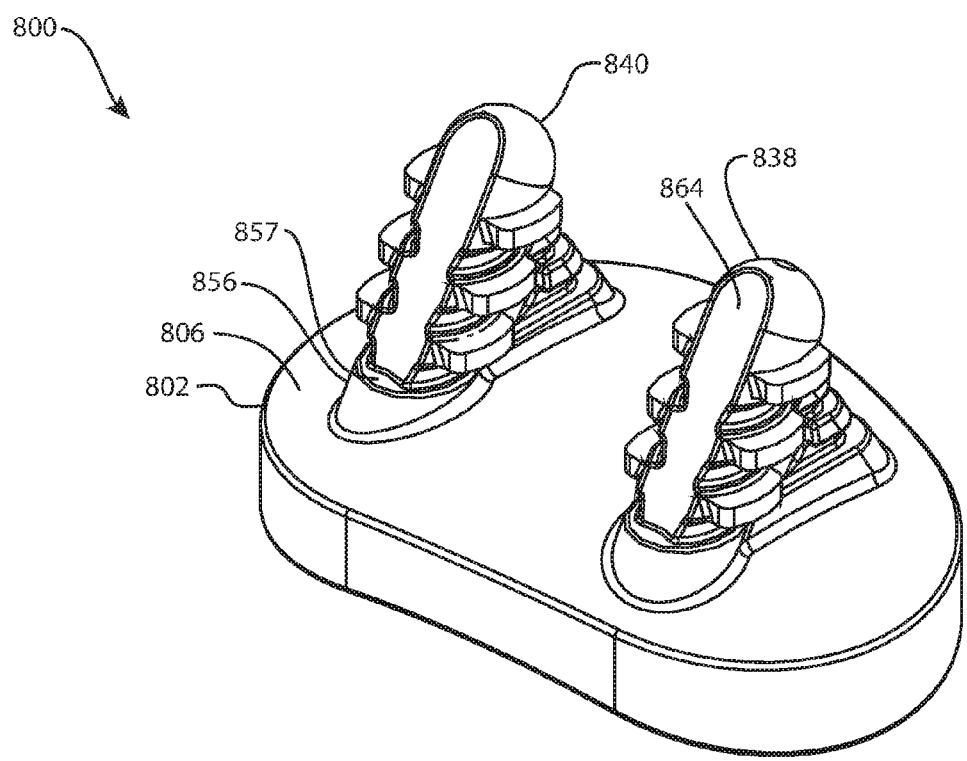
FIG. 1A is an isometric view of a left glenoid component.
Figure 1B:
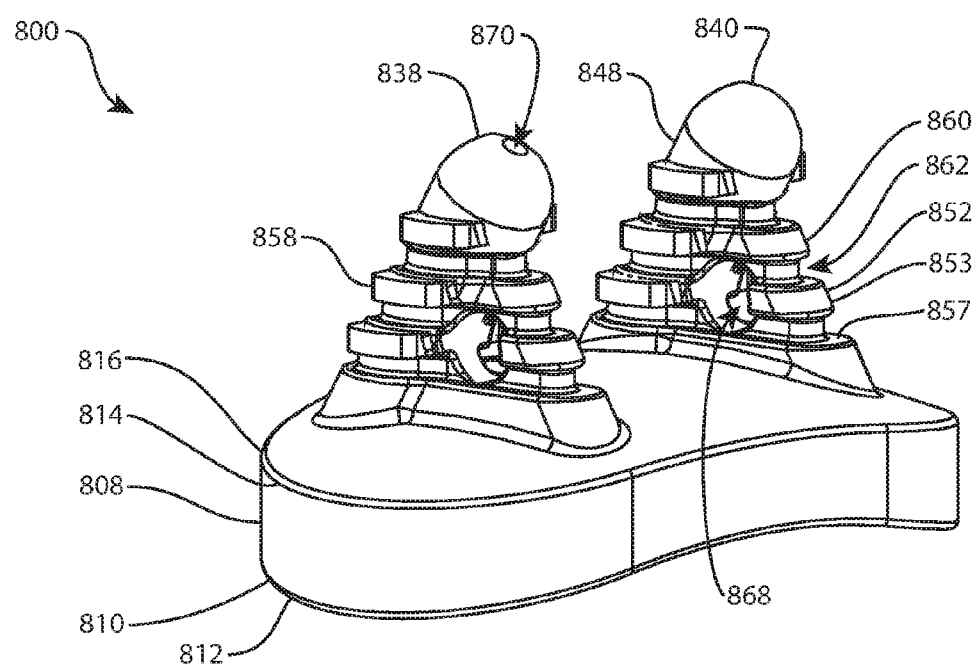
FIG. 1B is an oblique view of the glenoid component of FIG. 1A.
Figure 1C:
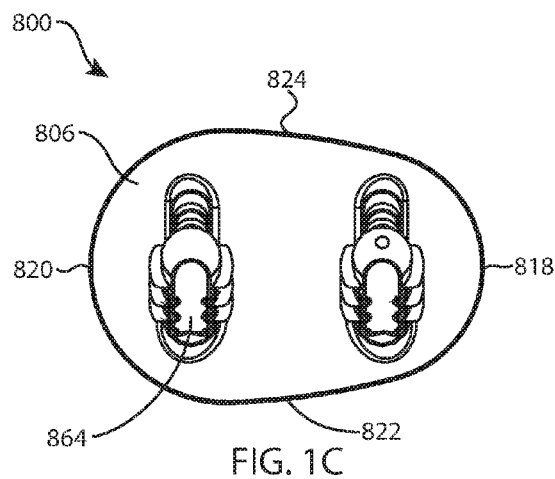
FIG. 1C is a medial view of the glenoid component of FIG. 1A.
Figure 1E:
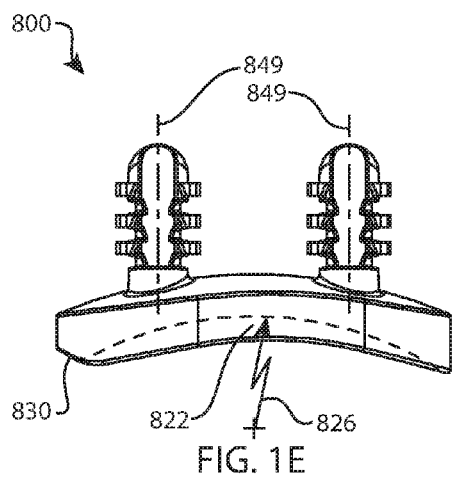
FIG. 1E is an anterior view of the glenoid component of FIG. 1A.
Figure 1D:
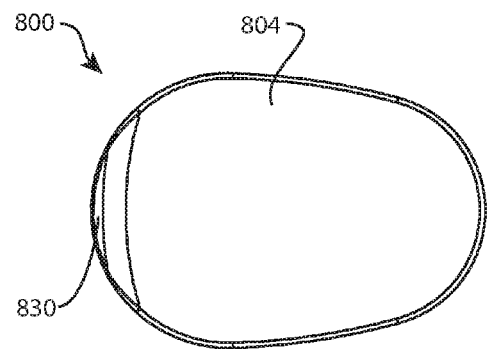
FIG. 1D is a lateral view of the glenoid component of FIG. 1A.
Figure 1F:
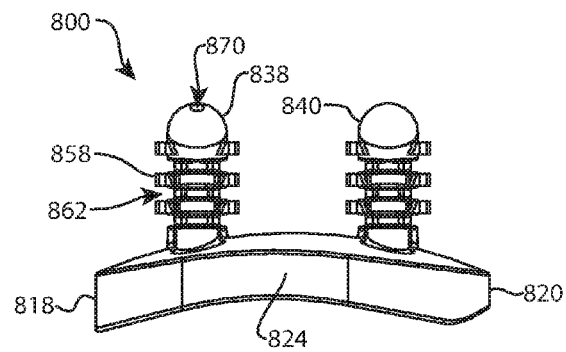
FIG. 1F is a posterior view of the glenoid component of FIG. 1A.
Figure 1G:
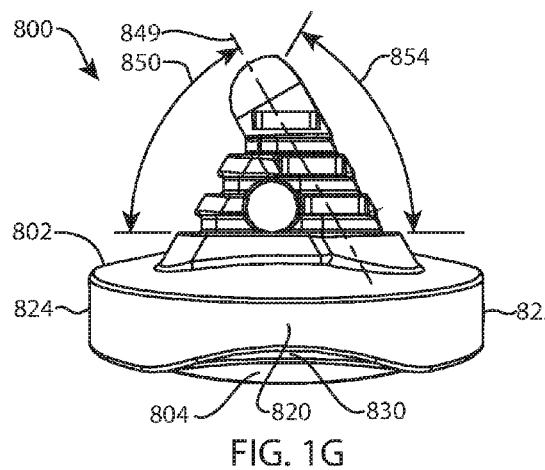
FIG. 1G is an inferior view of the glenoid component of FIG. 1A.
Figure 1H:
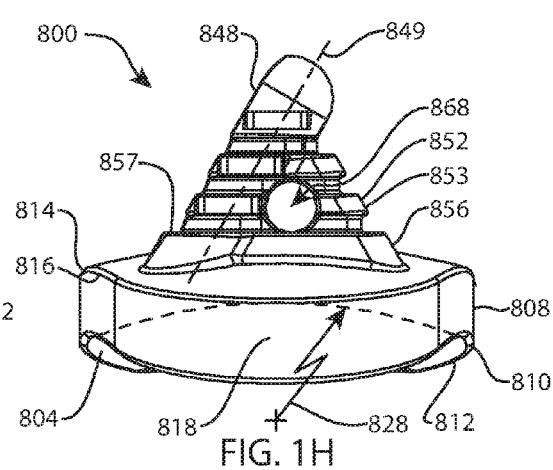
FIG. 1H is a superior view of the glenoid component of FIG. 1A.

Referring to FIGS. 1A-1H, a glenoid component 800 includes a body 802 with a lateral articular surface 804 and an opposite medial bone-facing surface 806.

A peripheral wall 808 extends around the body 802 between the surfaces 804, 806. A lateral peripheral edge 810 extends around the body 802 where the lateral articular surface 804 intersects the peripheral wall 808. The lateral peripheral edge 810 may be rounded or relieved by a lateral peripheral relief 812, such as a radius, fillet, chamfer, bevel, or the like. A medial peripheral edge 814 extends around the body 802 where the medial bone-facing surface 806 intersects the peripheral wall 808. The medial peripheral edge 814 may be rounded or relieved by a medial peripheral relief 816, such as a radius, fillet, chamfer, bevel, or the like.

The body 802, lateral articular surface 804, medial bone-facing surface 806, peripheral wall 808, lateral peripheral edge 810, lateral peripheral relief 812, medial peripheral edge 814, and/or medial peripheral relief 816 may be divided into a superior portion 818, an inferior portion 820, an anterior portion 822, and a posterior portion 824. The body 802, lateral articular surface 804, and/or medial bone-facing surface 806 may also be divided into a peripheral portion near the peripheral wall 808 and an interior or central portion. In examples other than shoulder glenoid components, where the surgical approach trajectory may be different than the approach described herein, the appropriate medical directional terms may be readily substituted by one of skill in the art.

The lateral articular surface 804 may be concave as shown, planar, or convex in order to complement a natural or prosthetic humeral articular surface. The lateral articular surface 804 may be spherical. The lateral articular surface 804 may be elliptical or ovoid. The lateral articular surface 804 may have a first radius 826 which is dimensionally different from, i.e., larger or smaller than, a second radius 828. The first radius 826 may be a superior-inferior radius, or S-I radius. The second radius 828 may be an anterior-posterior radius, or A-P radius.

The inferior portion 820 of the body 802 may include an inferior chamfer 830 which extends between the lateral articular surface 804 and the peripheral wall 808. The inferior chamfer 830 is a sloping surface, preferably a planar surface, that lowers the profile and thickness of the inferior portion 820 along the lateral peripheral edge 810.

The medial bone-facing surface 806 may be convex as shown, planar, or concave.

The glenoid component 800 includes at least one anchoring element 838 which protrudes outwardly from the medial bone-facing surface 806. The example shown includes a superior anchoring element 838 and an inferior anchoring element 840, although any number of anchoring elements may be present. Each anchoring element may be independently positioned on the medial bone-facing surface 806, and may be independently sized.

Each anchoring element 838, 840 includes a dowel 848, or mast, and a triangular reinforcement plate 852, or sail or buttress.

The dowel 848 projects from the medial bone-facing surface 806 at an angle 850 less than ninety degrees and greater than zero degrees. The angle 850 may be referred to as a dowel angle or a mast angle. The angle 850 may be measured between a central longitudinal axis 849 of the dowel 848 and a plane which is coplanar with the medial bone-facing surface 806, if surface 806 is planar, or a plane which is tangent to the medial bone-facing surface 806, if surface 806 is concave or convex. The plane may be tangent to the medial bone-facing surface 806 at an intersection point between the central longitudinal axis 849 of the dowel 848 and the medial bone-facing surface 806, or at a centroid of the medial bone-facing surface 806. The dowel 848 may project from the anterior portion 822 of the body 802, as shown, or from another portion of the body 802. In the example shown, the dowels 848 of anchoring elements 838, 840 project from peripheral locations in the anterior portion 822 and terminate in medially located free ends. The dowel 848 may have a round fundamental cross sectional shape, as shown, or another shape, such as a rectangle or dovetail. The dowel 848 may include a hole 870, which may receive a radiographic marker.

The reinforcement plate 852 projects from the medial bone-facing surface 806 in the acute angle 850 between the dowel 848 and the medial bone-facing surface 806, and coplanar with the dowel 848. An exposed side 853 of the reinforcement plate 852 projects from the medial bone-facing surface 806 at an angle 854 less than ninety degrees and greater than zero degrees. The angle 854 may be referred to as a reinforcement angle. The angle 854 opens toward the angle 850, and the sum of angles 850 and 854 is greater than zero degrees and less than one hundred eighty degrees. The reinforcement plate 852 intersects the dowel 848 to form a triangular shape with one side formed by the medial bone-facing surface 806, one side formed by the dowel 848, and one side formed by the exposed side 853 of the reinforcement plate 852. The triangular shape may be an acute triangle having three internal angles each less than 90 degrees.

The anchoring elements 838, 840 may include a pedestal 856 or footing where the anchoring element intersects the medial bone-facing surface 806. The pedestal 856 may be present on the dowel 848 or the reinforcement plate 852, or both. The pedestal 856 may enlarge the anchoring element 838, 840 at the medial bone-facing surface 806. The pedestal 856 may terminate medially in a planar face 857 which may establish the plane from which the angles 850, 854 are measured. The planar face 857 may be tangent to the medial bone-facing surface 806.

The anchoring elements 838, 840, including the dowels 848, the reinforcement plates 852, and the pedestals 856, may project outwardly from the medial bone-facing surface 806 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 838, and on the inferior side of the inferior anchoring element 840, or vice versa.

The anchoring elements 838, 840 may include surface features to improve fixation, or pull-out strength, after implantation. Surface features may be present on one or more of the anchoring elements present on a glenoid component. The surface features may project outwardly or inwardly from the fundamental surface(s) of the anchoring elements 838, 840. The surface features may include notches, grooves, channels, ridges, accordion texture, barbs, threads, shelves, rings, ribs, or perforations. For example, alternating ridges 860 and grooves 862 are shown, as well as fenestrations 868 extending through the anchoring elements 838, 840. The illustrated ridges 860 and grooves 862 are oriented to resist axial pull-out, i.e., forces acting perpendicular to the back side of the glenoid component, or the face 857 described below. The illustrated fenestrations 868 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 838 or 840. For example, the dowel 848 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 838, 840 to bend when inserted into the bone tunnel.

The anchoring elements 838, 840 may include at least two surface features, wherein the first surface feature is resistant to forces acting along a first direction, wherein the second surface feature is resistant to forces acting along a second direction, wherein the first and second directions are non-parallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 838, 840 may include one or more surface features that are resistant to side-to-side translation of the glenoid component 800, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring elements 838, 840 are illustrated with translation resistant surface features which are protruding shelves 858. The shelves 858 may protrude from the superior and/or inferior sides of each dowel 848 to increase the width of the dowel to resist translation. A total of twelve shelves 858 are shown, although any number may be present. The medial and lateral surfaces of the shelves 858 are parallel to the face 857 of the pedestal 856, so that the shelves 858 are oriented to resist axial pull-out, i.e., forces acting perpendicular to the back side of the glenoid component, or the face 857.

A slot 864, or groove or channel, may be present along the dowel, the exposed side 853 of the reinforcement plate 852, or both. In cemented applications of the technology, the bone cement may flow along the slot(s) 864 on the anchoring element.

The glenoid component 800 may be operatively implanted in a scapula 2 (not shown). The scapula 2 includes a glenoid fossa 4, a coracoid process 6, and an acromion process 8. The triangular shape of the anchoring elements 838, 840 matches the conical shape of the glenoid vault more closely than does a central peg or keel, in a superior-inferior view. The dowels 848 are peripherally arranged along the anterior portion 822 in the example shown. This places the pedestal 856 of the anchoring elements into regions of denser subchondral bone for stronger fixation. Medially in the glenoid vault, the side of the dowel 848 and the exposed side 853 of the reinforcement plate 852 may lie adjacent and parallel to the thick cortical walls of the glenoid vault.

Figure 2A:
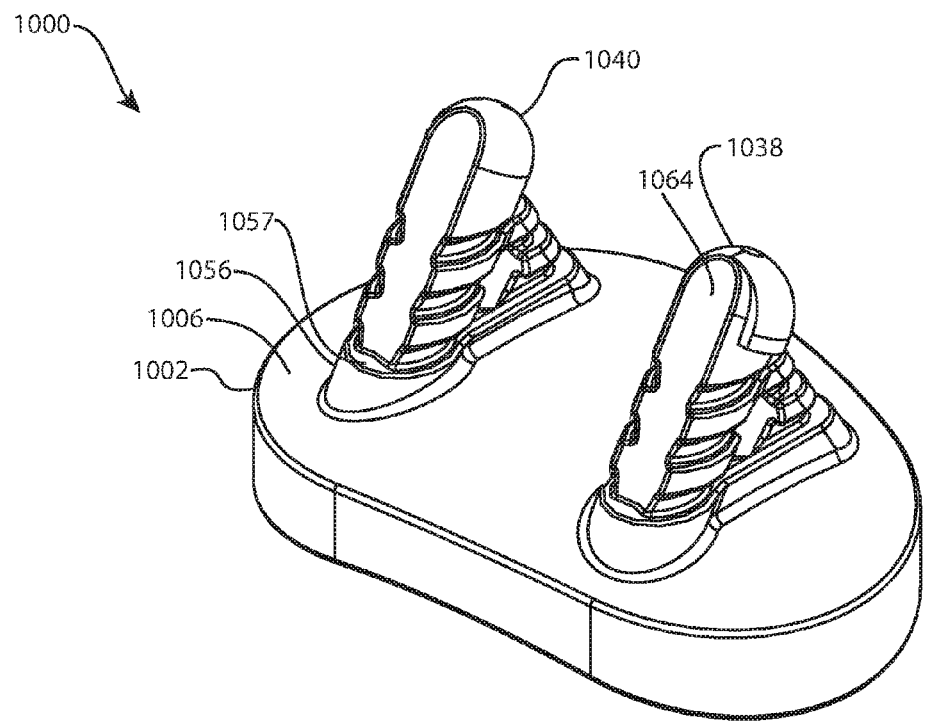
FIG. 2A is an isometric view of another left glenoid component.
Figure 2B:
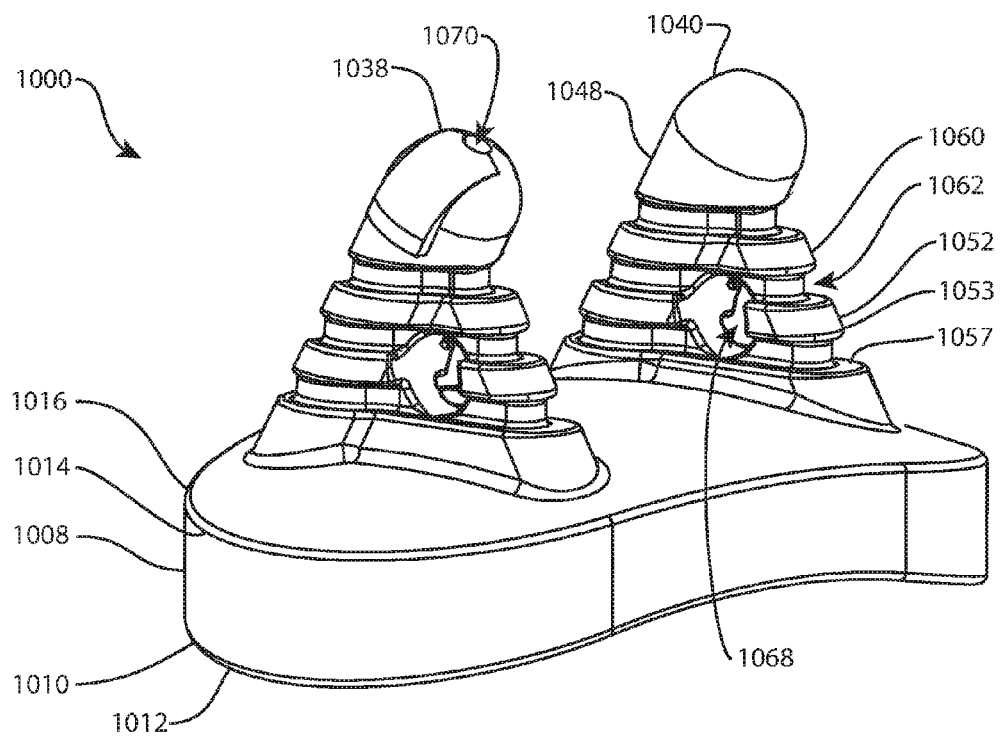
FIG. 2B is an oblique view of the glenoid component of FIG. 2A.
Figure 2C:
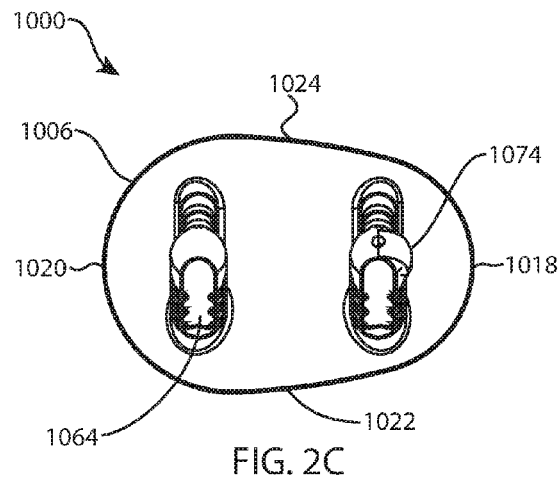
FIG. 2C is a medial view of the glenoid component of FIG. 2A.
Figure 2E:
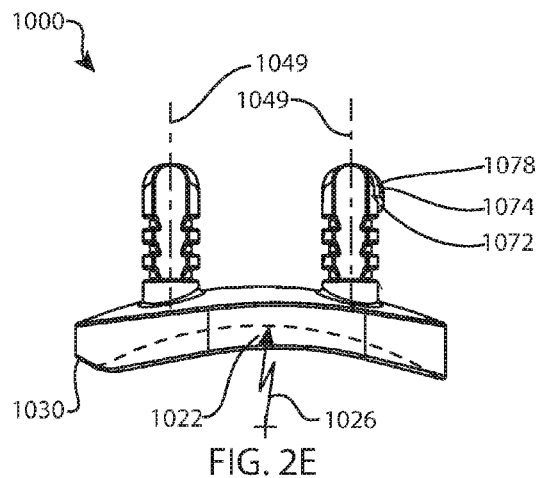
FIG. 2E is an anterior view of the glenoid component of FIG. 2A.
Figure 2D:
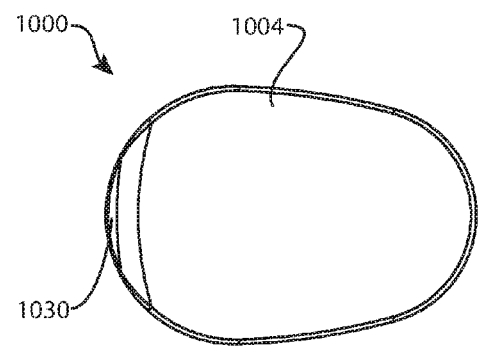
FIG. 2D is a lateral view of the glenoid component of FIG. 2A.
Figure 2F:
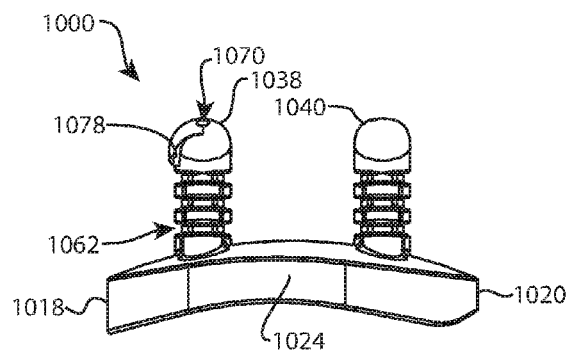
FIG. 2F is a posterior view of the glenoid component of FIG. 2A.
Figure 2G:
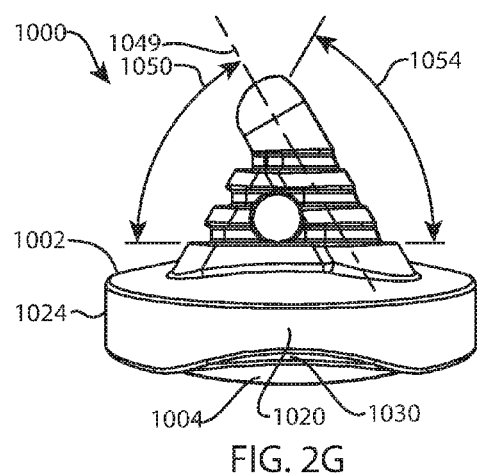
FIG. 2G is an inferior view of the glenoid component of FIG. 2A.
Figure 2H:
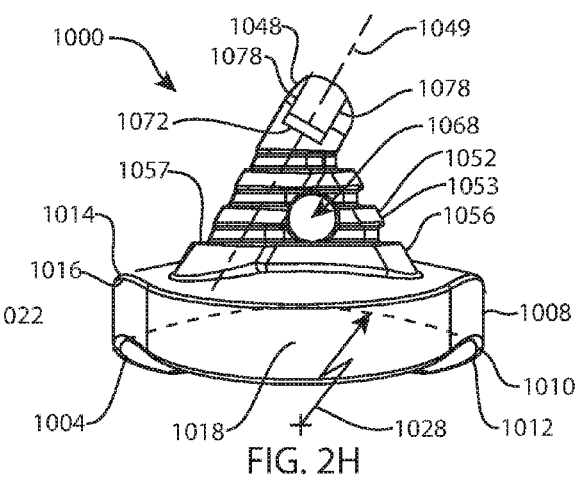
FIG. 2H is a superior view of the glenoid component of FIG. 2A.

Referring to FIGS. 2A-2H, a glenoid component 1000 includes a body 1002 with a lateral articular surface 1004 and an opposite medial bone-facing surface 1006.

A peripheral wall 1008 extends around the body 1002 between the surfaces 1004, 1006. A lateral peripheral edge 1010 extends around the body 1002 where the lateral articular surface 1004 intersects the peripheral wall 1008. The lateral peripheral edge 1010 may be rounded or relieved by a lateral peripheral relief 1012, such as a radius, fillet, chamfer, bevel, or the like. A medial peripheral edge 1014 extends around the body 1002 where the medial bone-facing surface 1006 intersects the peripheral wall 1008. The medial peripheral edge 1014 may be rounded or relieved by a medial peripheral relief 1016, such as a radius, fillet, chamfer, bevel, or the like.

The body 1002, lateral articular surface 1004, medial bone-facing surface 1006, peripheral wall 1008, lateral peripheral edge 1010, lateral peripheral relief 1012, medial peripheral edge 1014, and/or medial peripheral relief 1016 may be divided into a superior portion 1018, an inferior portion 1020, an anterior portion 1022, and a posterior portion 1024. The body 1002, lateral articular surface 1004, and/or medial bone-facing surface 1006 may also be divided into a peripheral portion near the peripheral wall 1008 and an interior or central portion. In examples other than shoulder glenoid components, where the surgical approach trajectory may be different than the approach described herein, the appropriate medical directional terms may be readily substituted by one of skill in the art.

The lateral articular surface 1004 may be concave as shown, planar, or convex in order to complement a natural or prosthetic humeral articular surface. The lateral articular surface 1004 may be spherical. The lateral articular surface 1004 may be elliptical or ovoid. The lateral articular surface 1004 may have a first radius 1026 which is dimensionally different from, i.e., larger or smaller than, a second radius 1028. The first radius 1026 may be a superior-inferior radius, or S-I radius. The second radius 1028 may be an anterior-posterior radius, or A-P radius.

The inferior portion 1020 of the body 1002 may include an inferior chamfer 1030 which extends between the lateral articular surface 1004 and the peripheral wall 1008. The inferior chamfer 1030 is a sloping surface, preferably a planar surface, that lowers the profile and thickness of the inferior portion 1020 along the lateral peripheral edge 1010.

The medial bone-facing surface 1006 may be convex as shown, planar, or concave.

The glenoid component 1000 includes at least one anchoring element 1038 which protrudes outwardly from the medial bone-facing surface 1006. The example shown includes a superior anchoring element 1038 and an inferior anchoring element 1040, although any number of anchoring elements may be present. Each anchoring element may be independently positioned on the medial bone-facing surface 1006, and may be independently sized.

Each anchoring element 1038, 1040 includes a dowel 1048, or mast, and a triangular reinforcement plate 1052, or sail or buttress.

The dowel 1048 projects from the medial bone-facing surface 1006 at an angle 1050 less than ninety degrees and greater than zero degrees. The angle 1050 may be referred to as a dowel angle or a mast angle. The angle 1050 may be measured between a central longitudinal axis 1049 of the dowel 1048 and a plane which is coplanar with the medial bone-facing surface 1006, if surface 1006 is planar, or a plane which is tangent to the medial bone-facing surface 1006, if surface 1006 is concave or convex. The plane may be tangent to the medial bone-facing surface 1006 at an intersection point between the central longitudinal axis 1049 of the dowel 1048 and the medial bone-facing surface 1006, or at a centroid of the medial bone-facing surface 1006. The dowel 1048 may project from the anterior portion 1022 of the body 1002, as shown, or from another portion of the body 1002. In the example shown, the dowels 1048 of anchoring elements 1038, 1040 project from peripheral locations in the anterior portion 1022 and terminate in medially located free ends. The dowel 1048 may have a round fundamental cross sectional shape, as shown, or another shape, such as a rectangle or dovetail. The dowel 1048 may include a hole 1070, which may receive a radiographic marker.

The reinforcement plate 1052 projects from the medial bone-facing surface 1006 in the acute angle 1050 between the dowel 1048 and the medial bone-facing surface 1006, and coplanar with the dowel 1048. An exposed side 1053 of the reinforcement plate 1052 projects from the medial bone-facing surface 1006 at an angle 1054 less than ninety degrees and greater than zero degrees. The angle 1054 may be referred to as a reinforcement angle. The angle 1054 opens toward the angle 1050, and the sum of angles 1050 and 1054 is greater than zero degrees and less than one hundred eighty degrees. The reinforcement plate 1052 intersects the dowel 1048 to form a triangular shape with one side formed by the medial bone-facing surface 1006, one side formed by the dowel 1048, and one side formed by the exposed side 1053 of the reinforcement plate 1052. The triangular shape may be an acute triangle having three internal angles each less than 90 degrees.

The anchoring elements 1038, 1040 may include a pedestal 1056 or footing where the anchoring element intersects the medial bone-facing surface 1006. The pedestal 1056 may be present on the dowel 1048 or the reinforcement plate 1052, or both. The pedestal 1056 may enlarge the anchoring element 1038, 1040 at the medial bone-facing surface 1006. The pedestal 1056 may terminate medially in a planar face 1057 which may establish the plane from which the angles 1050, 1054 are measured. The planar face 1057 may be tangent to the medial bone-facing surface 1006.

The anchoring elements 1038, 1040, including the dowels 1048, the reinforcement plates 1052, and the pedestals 1056, may project outwardly from the medial bone-facing surface 1006 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 1038, and on the inferior side of the inferior anchoring element 1040, or vice versa.

The anchoring elements 1038, 1040 may include surface features to improve fixation, or pull-out strength, after implantation. Surface features may be present on one or more of the anchoring elements present on a glenoid component. The surface features may project outwardly or inwardly from the fundamental surface(s) of the anchoring elements 1038, 1040. The surface features may include notches, grooves, channels, ridges, accordion texture, barbs, threads, shelves, rings, ribs, or perforations. For example, alternating ridges 1060 and grooves 1062 are shown, as well as fenestrations 1068 extending through the anchoring elements 1038, 1040. The illustrated ridges 1060 and grooves 1062 are oriented to resist axial pull-out, i.e., forces acting perpendicular to the back side of the glenoid component, or the face 1057 described below. The illustrated fenestrations 1068 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 1038 or 1040. For example, the dowel 1048 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 1038, 1040 to bend when inserted into the bone tunnel.

The anchoring elements 1038, 1040 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 1038, 1040 may include one or more surface features that are resistant to pullout forces acting along the central longitudinal axis 1049 of the dowel 1048. The anchoring element 1038 is illustrated with a surface feature which is a protruding planar surface 1072 which faces antero-laterally. The planar surface 1072 may protrude from the superior and/or inferior side of each dowel 1048 to increase the width of the dowel. One planar surface 1072 is shown protruding from the superior side of the dowel 1048 of the superior anchoring element 1038. The planar surface 1072 is perpendicular to the central longitudinal axis 1049 of the dowel 1048.

The anchoring elements 1038, 1040 may include one or more surface features that are resistant to pullout forces acting perpendicular to the central longitudinal axis 1049 of the dowel 1048. The anchoring element 1038 is illustrated with surface features which are protruding planar surfaces 1078. The planar surfaces 1078 may protrude from the anterior and/or posterior side of each dowel 1048 to increase the width of the dowel. Two planar surfaces 1078 are shown, with one planar surface 1078 facing antero-medially, and a second planar surface 1078 is shown facing postero-laterally, both on the superior anchoring element 1038. The planar surfaces 1078 are parallel to the central longitudinal axis 1049 of the dowel 1048.

The anchoring elements 1038, 1040 may include one or more surface features that are resistant to side-to-side translation of the glenoid component 1000, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 1038 is illustrated with a translation resistant surface feature which is a protruding dowel tip 1074, which is enlarged relative to the fundamental surface of the dowel 1048. The dowel tip 1074 may protrude from the superior, inferior, anterior, and/or posterior side of each dowel 1048, or intermediate positions such as superior-posterior, to increase the width of the dowel to resist translation. One dowel tip 1074 is shown protruding from the superior side of the dowel 1048 of the superior anchoring element 1038. The dowel tip 1074 terminates with the antero-laterally facing planar surface 1072, the antero-medially facing planar surface 1078, and the postero-laterally facing planar surface 1078. The interaction of the dowel tip 1074 and the bone tunnel mouth may cause the anchoring element 1038 to bend toward the anchoring element 1040 as the dowel tip 1074 is inserted in the bone tunnel.

A slot 1064, or groove or channel, may be present along the dowel, the exposed side 1053 of the reinforcement plate 1052, or both. In cemented applications of the technology, the bone cement may flow along the slot(s) 1064 on the anchoring element.

The glenoid component 1000 may be operatively implanted in a scapula 2 (not shown). The scapula 2 includes a glenoid fossa 4, a coracoid process 6, and an acromion process 8. The triangular shape of the anchoring elements 1038, 1040 matches the conical shape of the glenoid vault more closely than does a central peg or keel, in a superior-inferior view. The dowels 1048 are peripherally arranged along the anterior portion 1022 in the example shown. This places the pedestal 1056 of the anchoring elements into regions of denser subchondral bone for stronger fixation. Medially in the glenoid vault, the side of the dowel 1048 and the exposed side 1053 of the reinforcement plate 1052 may lie adjacent and parallel to the thick cortical walls of the glenoid vault.

Figure 3A:
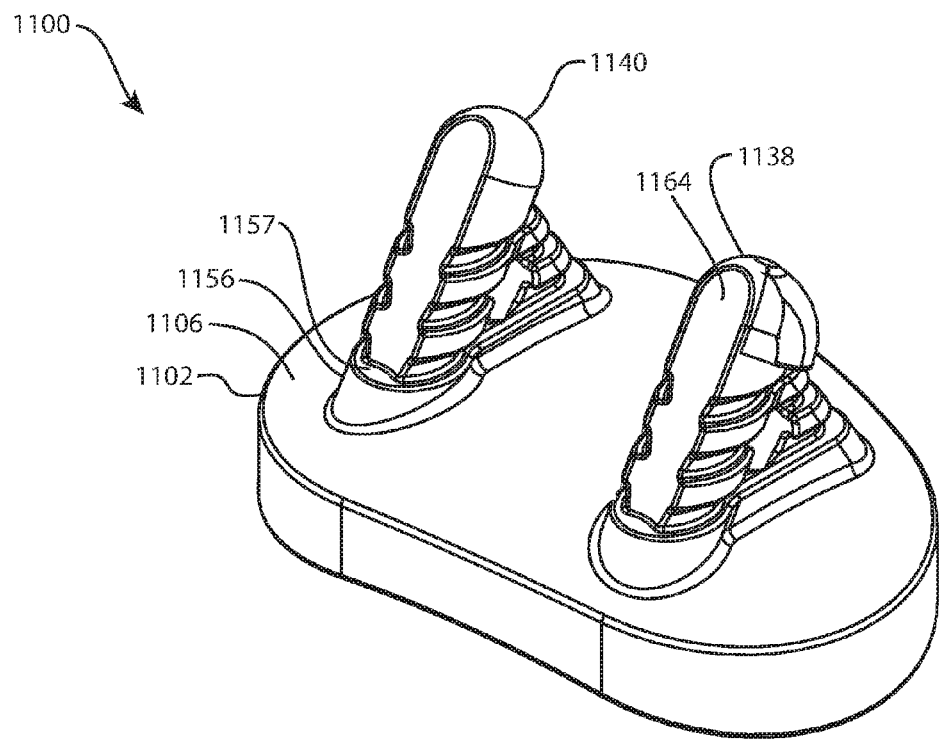
FIG. 3A is an isometric view of yet another left glenoid component.
Figure 3B:
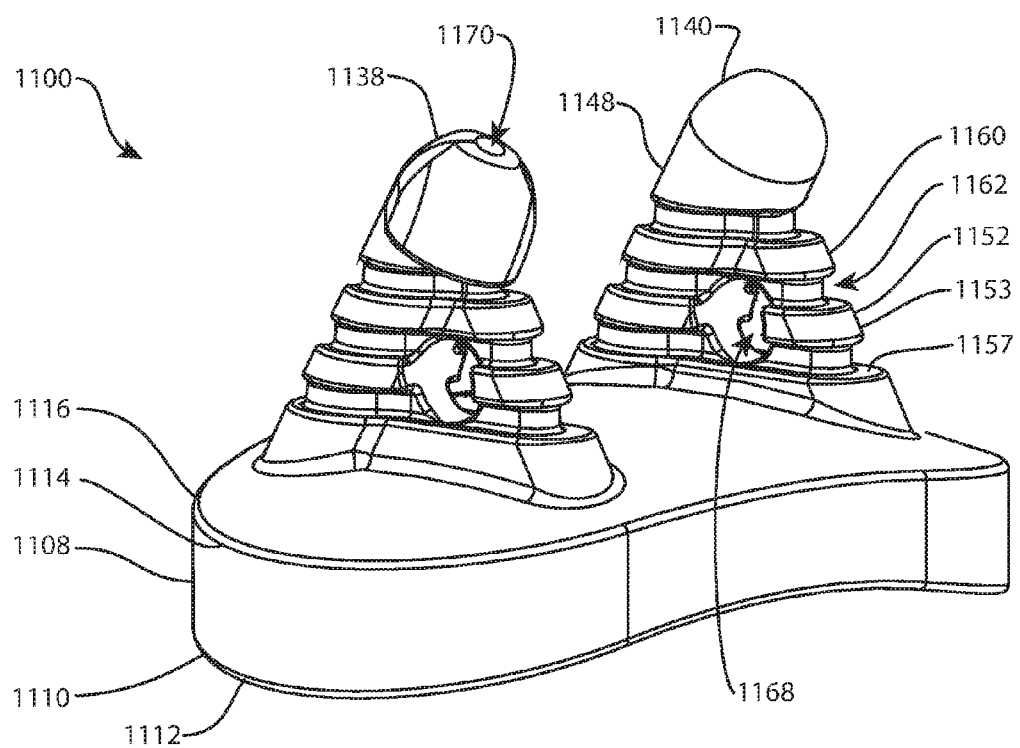
FIG. 3B is an oblique view of the glenoid component of FIG. 3A.
Figure 3C:
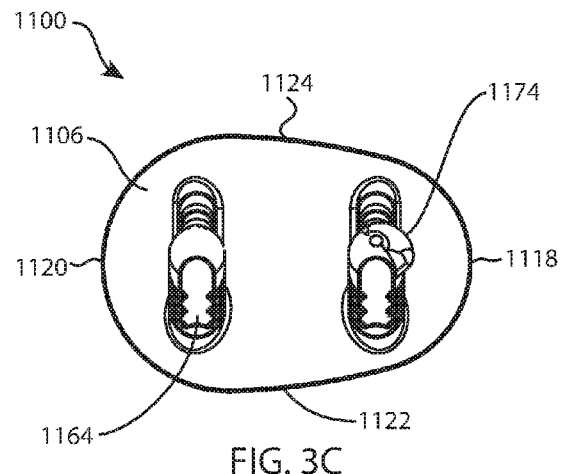
FIG. 3C is a medial view of the glenoid component of FIG. 3A.
Figure 3E:
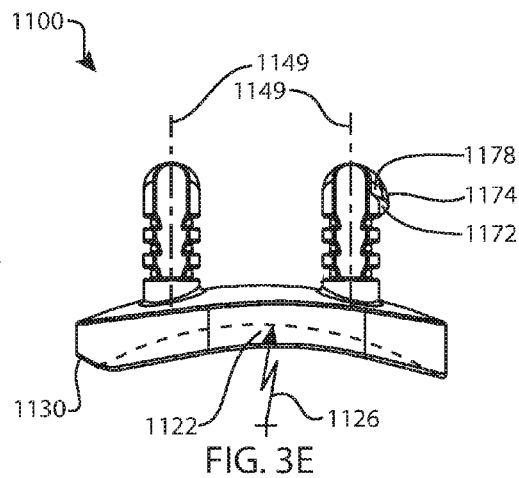
FIG. 3E is an anterior view of the glenoid component of FIG. 3A.
Figure 3D:
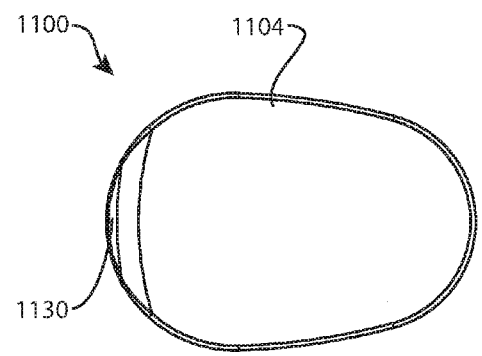
FIG. 3D is a lateral view of the glenoid component of FIG. 3A.
Figure 3F:
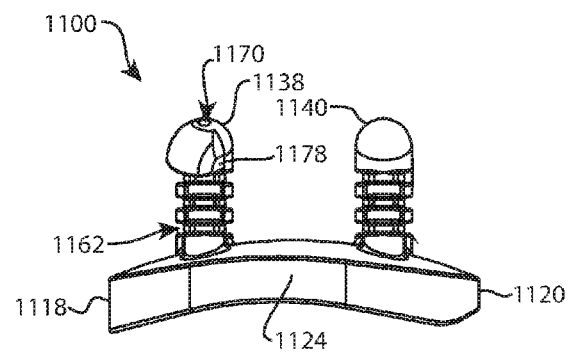
FIG. 3F is a posterior view of the glenoid component of FIG. 3A.
Figure 3G:
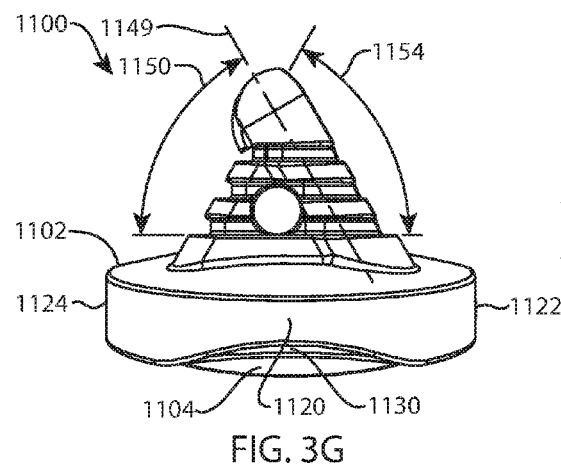
FIG. 3G is an inferior view of the glenoid component of FIG. 3A.
Figure 3H:
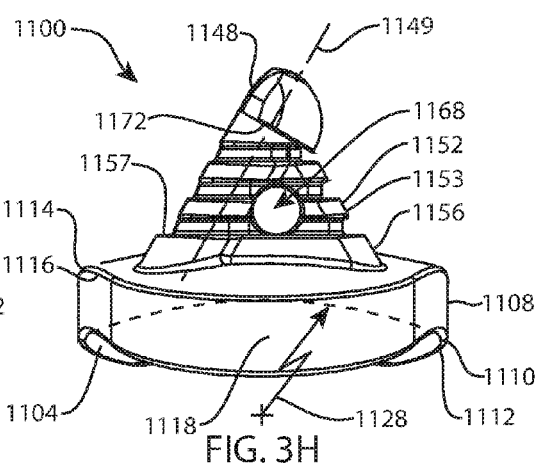
FIG. 3H is a superior view of the glenoid component of FIG. 3A.

Referring to FIGS. 3A-3H, a glenoid component 1100 includes a body 1102 with a lateral articular surface 1104 and an opposite medial bone-facing surface 1106.

A peripheral wall 1108 extends around the body 1102 between the surfaces 1104, 1106. A lateral peripheral edge 1110 extends around the body 1102 where the lateral articular surface 1104 intersects the peripheral wall 1108. The lateral peripheral edge 1110 may be rounded or relieved by a lateral peripheral relief 1112, such as a radius, fillet, chamfer, bevel, or the like. A medial peripheral edge 1114 extends around the body 1102 where the medial bone-facing surface 1106 intersects the peripheral wall 1108. The medial peripheral edge 1114 may be rounded or relieved by a medial peripheral relief 1116, such as a radius, fillet, chamfer, bevel, or the like.

The body 1102, lateral articular surface 1104, medial bone-facing surface 1106, peripheral wall 1108, lateral peripheral edge 1110, lateral peripheral relief 1112, medial peripheral edge 1114, and/or medial peripheral relief 1116 may be divided into a superior portion 1118, an inferior portion 1120, an anterior portion 1122, and a posterior portion 1124. The body 1102, lateral articular surface 1104, and/or medial bone-facing surface 1106 may also be divided into a peripheral portion near the peripheral wall 1108 and an interior or central portion. In examples other than shoulder glenoid components, where the surgical approach trajectory may be different than the approach described herein, the appropriate medical directional terms may be readily substituted by one of skill in the art.

The lateral articular surface 1104 may be concave as shown, planar, or convex in order to complement a natural or prosthetic humeral articular surface. The lateral articular surface 1104 may be spherical. The lateral articular surface 1104 may be elliptical or ovoid. The lateral articular surface 1104 may have a first radius 1126 which is dimensionally different from, i.e., larger or smaller than, a second radius 1128. The first radius 1126 may be a superior-inferior radius, or S-I radius. The second radius 1128 may be an anterior-posterior radius, or A-P radius.

The inferior portion 1120 of the body 1102 may include an inferior chamfer 1130 which extends between the lateral articular surface 1104 and the peripheral wall 1108. The inferior chamfer 1130 is a sloping surface, preferably a planar surface, that lowers the profile and thickness of the inferior portion 1120 along the lateral peripheral edge 1110.

The medial bone-facing surface 1106 may be convex as shown, planar, or concave.

The glenoid component 1100 includes at least one anchoring element 1138 which protrudes outwardly from the medial bone-facing surface 1106. The example shown includes a superior anchoring element 1138 and an inferior anchoring element 1140, although any number of anchoring elements may be present. Each anchoring element may be independently positioned on the medial bone-facing surface 1106, and may be independently sized.

Each anchoring element 1138, 1140 includes a dowel 1148, or mast, and a triangular reinforcement plate 1152, or sail or buttress.

The dowel 1148 projects from the medial bone-facing surface 1106 at an angle 1150 less than ninety degrees and greater than zero degrees. The angle 1150 may be referred to as a dowel angle or a mast angle. The angle 1150 may be measured between a central longitudinal axis 1149 of the dowel 1148 and a plane which is coplanar with the medial bone-facing surface 1106, if surface 1106 is planar, or a plane which is tangent to the medial bone-facing surface 1106, if surface 1106 is concave or convex. The plane may be tangent to the medial bone-facing surface 1106 at an intersection point between the central longitudinal axis 1149 of the dowel 1148 and the medial bone-facing surface 1106, or at a centroid of the medial bone-facing surface 1106. The dowel 1148 may project from the anterior portion 1122 of the body 1102, as shown, or from another portion of the body 1102. In the example shown, the dowels 1148 of anchoring elements 1138, 1140 project from peripheral locations in the anterior portion 1122 and terminate in medially located free ends. The dowel 1148 may have a round fundamental cross sectional shape, as shown, or another shape, such as a rectangle or dovetail. The dowel 1148 may include a hole 1170, which may receive a radiographic marker.

The reinforcement plate 1152 projects from the medial bone-facing surface 1106 in the acute angle 1150 between the dowel 1148 and the medial bone-facing surface 1106, and coplanar with the dowel 1148. An exposed side 1153 of the reinforcement plate 1152 projects from the medial bone-facing surface 1106 at an angle 1154 less than ninety degrees and greater than zero degrees. The angle 1154 may be referred to as a reinforcement angle. The angle 1154 opens toward the angle 1150, and the sum of angles 1150 and 1154 is greater than zero degrees and less than one hundred eighty degrees. The reinforcement plate 1152 intersects the dowel 1148 to form a triangular shape with one side formed by the medial bone-facing surface 1106, one side formed by the dowel 1148, and one side formed by the exposed side 1153 of the reinforcement plate 1152. The triangular shape may be an acute triangle having three internal angles each less than 90 degrees.

The anchoring elements 1138, 1140 may include a pedestal 1156 or footing where the anchoring element intersects the medial bone-facing surface 1106. The pedestal 1156 may be present on the dowel 1148 or the reinforcement plate 1152, or both. The pedestal 1156 may enlarge the anchoring element 1138, 1140 at the medial bone-facing surface 1106. The pedestal 1156 may terminate medially in a planar face 1157 which may establish the plane from which the angles 1150, 1154 are measured. The planar face 1157 may be tangent to the medial bone-facing surface 1106.

The anchoring elements 1138, 1140, including the dowels 1148, the reinforcement plates 1152, and the pedestals 1156, may project outwardly from the medial bone-facing surface 1106 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 1138, and on the inferior side of the inferior anchoring element 1140, or vice versa.

The anchoring elements 1138, 1140 may include surface features to improve fixation, or pull-out strength, after implantation. Surface features may be present on one or more of the anchoring elements present on a glenoid component. The surface features may project outwardly or inwardly from the fundamental surface(s) of the anchoring elements 1138, 1140. The surface features may include notches, grooves, channels, ridges, accordion texture, barbs, threads, shelves, rings, ribs, or perforations. For example, alternating ridges 1160 and grooves 1162 are shown, as well as fenestrations 1168 extending through the anchoring elements 1138, 1140. The illustrated ridges 1160 and grooves 1162 are oriented to resist axial pull-out, i.e., forces acting perpendicular to the back side of the glenoid component, or the face 1157 described below. The illustrated fenestrations 1168 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 1138 or 1140. For example, the dowel 1148 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 1138, 1140 to bend when inserted into the bone tunnel.

The anchoring elements 1138, 1140 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 1138, 1140 may include one or more surface features that are resistant to pullout forces acting along the central longitudinal axis 1149 of the dowel 1148. The anchoring element 1138 is illustrated with a surface feature which is a protruding planar surface 1172 which faces antero-laterally. The planar surface 1172 may protrude from the superior and/or inferior side of each dowel 1148 to increase the width of the dowel. One planar surface 1172 is shown protruding from the superior-posterior side of the dowel 1148 of the superior anchoring element 1138. The planar surface 1172 is perpendicular to the central longitudinal axis 1149 of the dowel 1148.

The anchoring elements 1138, 1140 may include one or more surface features that are resistant to pullout forces acting perpendicular to the central longitudinal axis 1149 of the dowel 1148. The anchoring element 1138 is illustrated with surface features which are protruding planar surfaces 1178. The planar surfaces 1178 may protrude from the anterior and/or posterior side of each dowel 1148 to increase the width of the dowel. Two planar surfaces 1178 are shown, with one planar surface 1178 facing antero-medially, and a second planar surface 1178 is shown facing postero-laterally, both on the superior anchoring element 1138. The planar surfaces 1178 are parallel to the central longitudinal axis 1149 of the dowel 1148.

The anchoring elements 1138, 1140 may include one or more surface features that are resistant to side-to-side translation of the glenoid component 1100, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 1138 is illustrated with a translation resistant surface feature which is a protruding dowel tip 1174, which is enlarged relative to the fundamental surface of the dowel 1148. The dowel tip 1174 may protrude from the superior and/or inferior side of each dowel 1148 to increase the width of the dowel to resist translation. One dowel tip 1174 is shown protruding from the superior-posterior side of the dowel 1148 of the superior anchoring element 1138. The dowel tip 1174 terminates with the antero-laterally facing planar surface 1172, the antero-medially facing planar surface 1178, and the postero-laterally facing planar surface 1178. The interaction of the dowel tip 1174 and the bone tunnel mouth may cause the anchoring element 1138 to bend toward the anchoring element 1140 as the dowel tip 1174 is inserted in the bone tunnel.

A slot 1164, or groove or channel, may be present along the dowel, the exposed side 1153 of the reinforcement plate 1152, or both. In cemented applications of the technology, the bone cement may flow along the slot(s) 1164 on the anchoring element.

The glenoid component 1100 may be operatively implanted in a scapula 2 (not shown). The scapula 2 includes a glenoid fossa 4, a coracoid process 6, and an acromion process 8. The triangular shape of the anchoring elements 1138, 1140 matches the conical shape of the glenoid vault more closely than does a central peg or keel, in a superior-inferior view. The dowels 1148 are peripherally arranged along the anterior portion 1122 in the example shown. This places the pedestal 1156 of the anchoring elements into regions of denser subchondral bone for stronger fixation. Medially in the glenoid vault, the side of the dowel 1148 and the exposed side 1153 of the reinforcement plate 1152 may lie adjacent and parallel to the thick cortical walls of the glenoid vault.

Figure 4A:
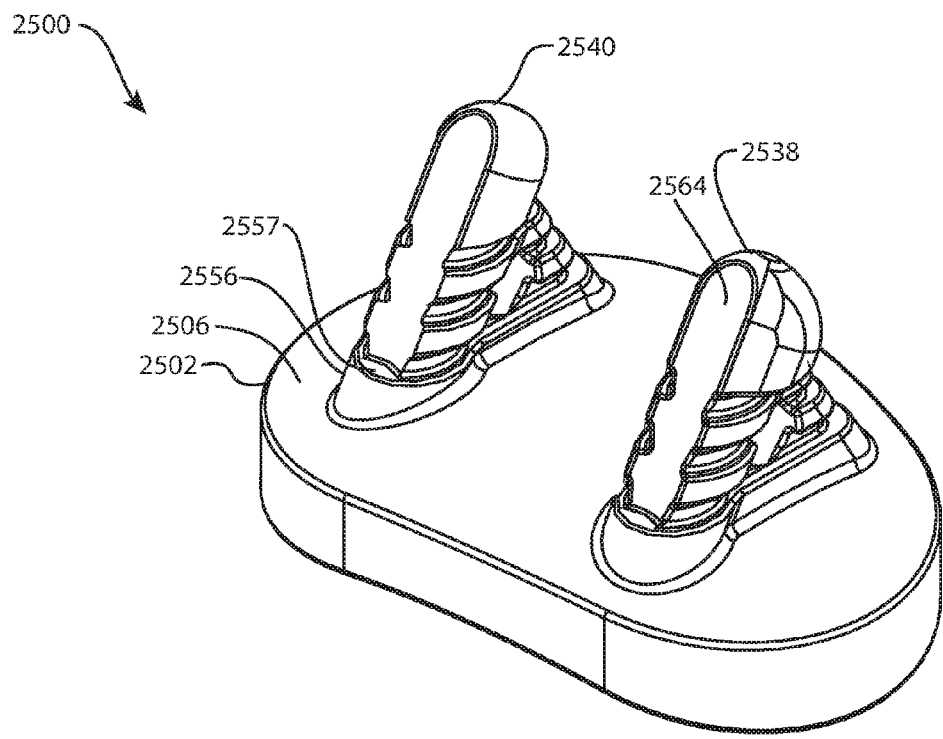
FIG. 4A is an isometric view of yet another left glenoid component.
Figure 4B:
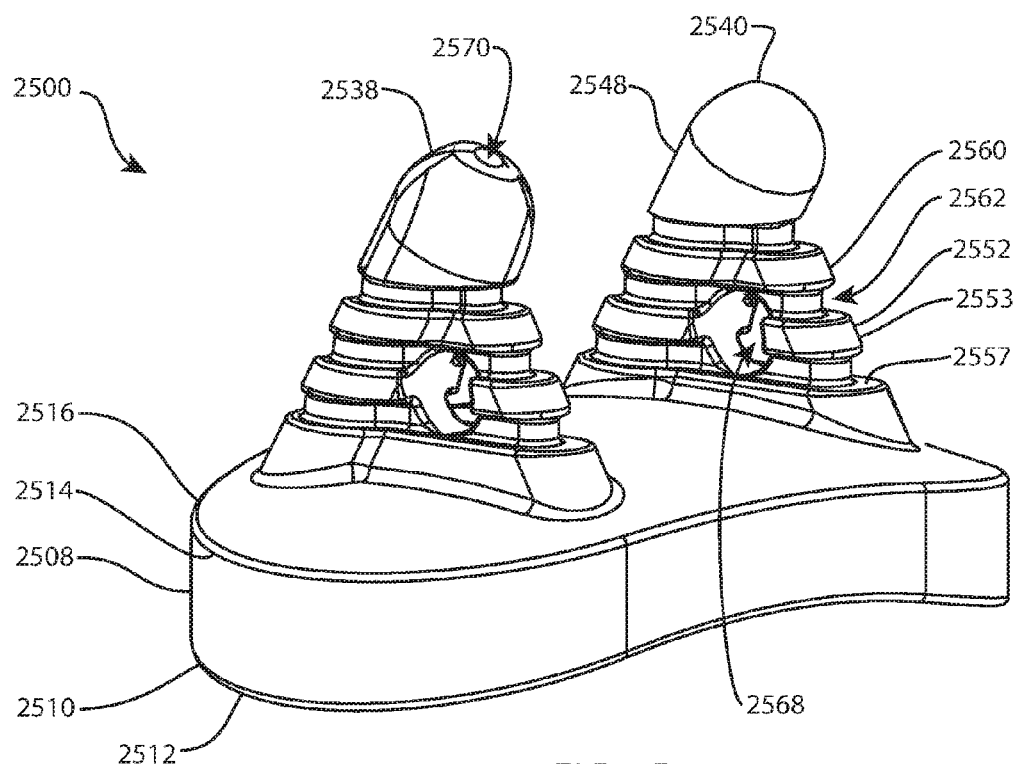
FIG. 4B is an oblique view of the glenoid component of FIG. 4A.
Figure 4C:
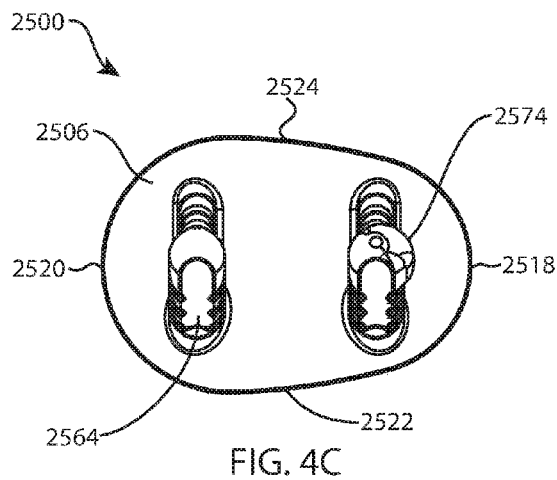
FIG. 4C is a medial view of the glenoid component of FIG. 4A.
Figure 4E:
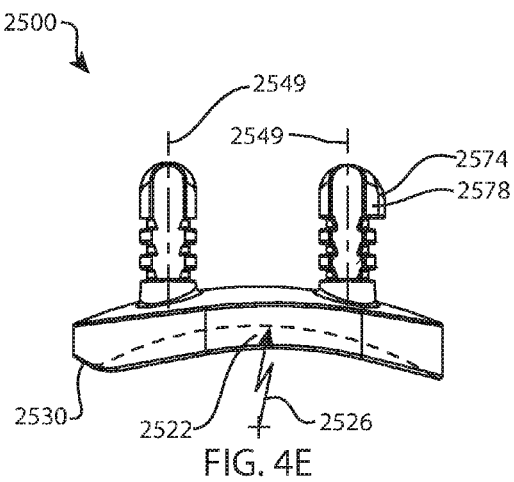
FIG. 4E is an anterior view of the glenoid component of FIG. 4A.
Figure 4D:
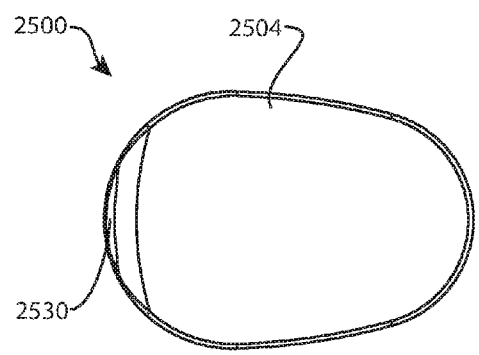
FIG. 4D is a lateral view of the glenoid component of FIG. 4A.
Figure 4F:
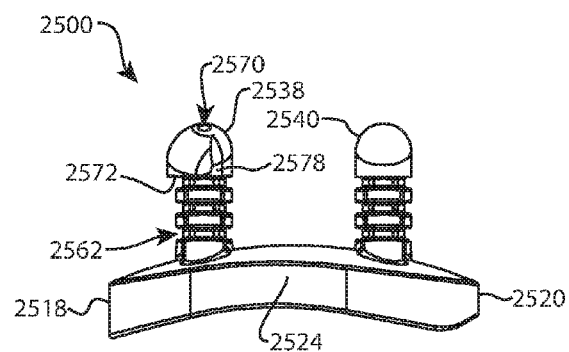
FIG. 4F is a posterior view of the glenoid component of FIG. 4A.
Figure 4G:
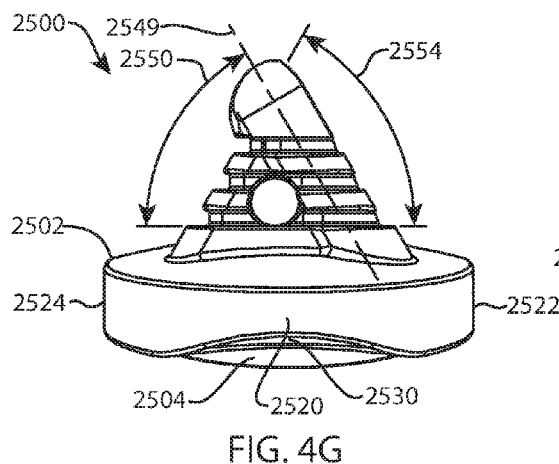
FIG. 4G is an inferior view of the glenoid component of FIG. 4A.
Figure 4H:
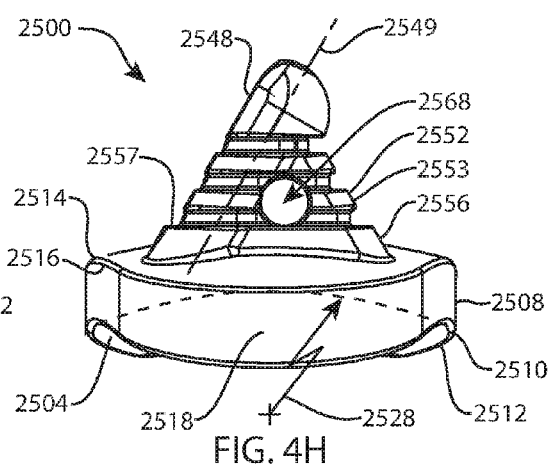
FIG. 4H is a superior view of the glenoid component of FIG. 4A.

Referring to FIGS. 4A-4H, a glenoid component 2500 includes a body 2502 with a lateral articular surface 2504 and an opposite medial bone-facing surface 2506.

A peripheral wall 2508 extends around the body 2502 between the surfaces 2504, 2506. A lateral peripheral edge 2510 extends around the body 2502 where the lateral articular surface 2504 intersects the peripheral wall 2508. The lateral peripheral edge 2510 may be rounded or relieved by a lateral peripheral relief 2512, such as a radius, fillet, chamfer, bevel, or the like. A medial peripheral edge 2514 extends around the body 2502 where the medial bone-facing surface 2506 intersects the peripheral wall 2508. The medial peripheral edge 2514 may be rounded or relieved by a medial peripheral relief 2516, such as a radius, fillet, chamfer, bevel, or the like.

The body 2502, lateral articular surface 2504, medial bone-facing surface 2506, peripheral wall 2508, lateral peripheral edge 2510, lateral peripheral relief 2512, medial peripheral edge 2514, and/or medial peripheral relief 2516 may be divided into a superior portion 2518, an inferior portion 2520, an anterior portion 2522, and a posterior portion 2524. The body 2502, lateral articular surface 2504, and/or medial bone-facing surface 2506 may also be divided into a peripheral portion near the peripheral wall 2508 and an interior or central portion. In examples other than shoulder glenoid components, where the surgical approach trajectory may be different than the approach described herein, the appropriate medical directional terms may be readily substituted by one of skill in the art.

The lateral articular surface 2504 may be concave as shown, planar, or convex in order to complement a natural or prosthetic humeral articular surface. The lateral articular surface 2504 may be spherical. The lateral articular surface 2504 may be elliptical or ovoid. The lateral articular surface 2504 may have a first radius 2526 which is dimensionally different from, i.e., larger or smaller than, a second radius 2528. The first radius 2526 may be a superior-inferior radius, or S-I radius. The second radius 2528 may be an anterior-posterior radius, or A-P radius.

The inferior portion 2520 of the body 2502 may include an inferior chamfer 2530 which extends between the lateral articular surface 2504 and the peripheral wall 2508. The inferior chamfer 2530 is a sloping surface, preferably a planar surface, that lowers the profile and thickness of the inferior portion 2520 along the lateral peripheral edge 2510.

The medial bone-facing surface 2506 may be convex as shown, planar, or concave.

The glenoid component 2500 includes at least one anchoring element 2538 which protrudes outwardly from the medial bone-facing surface 2506. The example shown includes a superior anchoring element 2538 and an inferior anchoring element 2540, although any number of anchoring elements may be present. Each anchoring element may be independently positioned on the medial bone-facing surface 2506, and may be independently sized.

Each anchoring element 2538, 2540 includes a dowel 2548, or mast, and a triangular reinforcement plate 2552, or sail or buttress.

The dowel 2548 projects from the medial bone-facing surface 2506 at an angle 2550 less than ninety degrees and greater than zero degrees. The angle 2550 may be referred to as a dowel angle or a mast angle. The angle 2550 may be measured between a central longitudinal axis 2549 of the dowel 2548 and a plane which is coplanar with the medial bone-facing surface 2506, if surface 2506 is planar, or a plane which is tangent to the medial bone-facing surface 2506, if surface 2506 is concave or convex. The plane may be tangent to the medial bone-facing surface 2506 at an intersection point between the central longitudinal axis 2549 of the dowel 2548 and the medial bone-facing surface 2506, or at a centroid of the medial bone-facing surface 2506. The dowel 2548 may project from the anterior portion 2522 of the body 2502, as shown, or from another portion of the body 2502. In the example shown, the dowels 2548 of anchoring elements 2538, 2540 project from peripheral locations in the anterior portion 2522 and terminate in medially located free ends. The dowel 2548 may have a round fundamental cross sectional shape, as shown, or another shape, such as a rectangle or dovetail. The dowel 2548 may include a hole 2570, which may receive a radiographic marker.

The reinforcement plate 2552 projects from the medial bone-facing surface 2506 in the acute angle 2550 between the dowel 2548 and the medial bone-facing surface 2506, and coplanar with the dowel 2548. An exposed side 2553 of the reinforcement plate 2552 projects from the medial bone-facing surface 2506 at an angle 2554 less than ninety degrees and greater than zero degrees. The angle 2554 may be referred to as a reinforcement angle. The angle 2554 opens toward the angle 2550, and the sum of angles 2550 and 2554 is greater than zero degrees and less than one hundred eighty degrees. The reinforcement plate 2552 intersects the dowel 2548 to form a triangular shape with one side formed by the medial bone-facing surface 2506, one side formed by the dowel 2548, and one side formed by the exposed side 2553 of the reinforcement plate 2552. The triangular shape may be an acute triangle having three internal angles each less than 90 degrees.

The anchoring elements 2538, 2540 may include a pedestal 2556 or footing where the anchoring element intersects the medial bone-facing surface 2506. The pedestal 2556 may be present on the dowel 2548 or the reinforcement plate 2552, or both. The pedestal 2556 may enlarge the anchoring element 2538, 2540 at the medial bone-facing surface 2506. The pedestal 2556 may terminate medially in a planar face 2557 which may establish the plane from which the angles 2550, 2554 are measured. The planar face 2557 may be tangent to the medial bone-facing surface 2506.

The anchoring elements 2538, 2540, including the dowels 2548, the reinforcement plates 2552, and the pedestals 2556, may project outwardly from the medial bone-facing surface 2506 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 2538, and on the inferior side of the inferior anchoring element 2540, or vice versa.

The anchoring elements 2538, 2540 may include surface features to improve fixation, or pull-out strength, after implantation. Surface features may be present on one or more of the anchoring elements present on a glenoid component. The surface features may project outwardly or inwardly from the fundamental surface(s) of the anchoring elements 2538, 2540. The surface features may include notches, grooves, channels, ridges, accordion texture, barbs, threads, shelves, rings, ribs, or perforations. For example, alternating ridges 2560 and grooves 2562 are shown, as well as fenestrations 2568 extending through the anchoring elements 2538, 2540. The illustrated ridges 2560 and grooves 2562 are oriented to resist axial pull-out, i.e., forces acting perpendicular to the back side of the glenoid component, or the face 2557 described below. The illustrated fenestrations 2568 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 2538 or 2540. For example, the dowel 2548 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 2538, 2540 to bend when inserted into the bone tunnel.

The anchoring elements 2538, 2540 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 2538, 2540 may include one or more surface features that are resistant to axial pull-out, i.e., forces acting perpendicular to the back side of the glenoid component, or the face 2557. The anchoring element 2538 is illustrated with a surface feature which is a protruding planar surface 2572 which faces laterally. The planar surface 2572 may protrude from the superior and/or inferior side of each dowel 2548 to increase the width of the dowel. One planar surface 2572 is shown protruding from the superior-posterior side of the dowel 2548 of the superior anchoring element 2538. The planar surface 2572 is parallel to the face 2557 of the pedestal 2556.

The anchoring elements 2538, 2540 may include one or more surface features that are resistant to pullout forces acting perpendicular to the central longitudinal axis 2549 of the dowel 2548. The anchoring element 2538 is illustrated with surface features which are protruding planar surfaces 2578. The planar surfaces 2578 may protrude from the anterior and/or posterior side of each dowel 2548 to increase the width of the dowel. Two planar surfaces 2578 are shown, with one planar surface 2578 facing antero-medially, and a second planar surface 2578 is shown facing postero-laterally, both on the superior anchoring element 2538. The planar surfaces 2578 are parallel to the central longitudinal axis 2549 of the dowel 2548.

The anchoring elements 2538, 2540 may include one or more surface features that are resistant to side-to-side translation of the glenoid component 2500, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 2538 is illustrated with a translation resistant surface feature which is a protruding dowel tip 2574, which is enlarged relative to the fundamental surface of the dowel 2548. The dowel tip 2574 may protrude from the superior and/or inferior side of each dowel 2548 to increase the width of the dowel to resist translation. One dowel tip 2574 is shown protruding from the superior-posterior side of the dowel 2548 of the superior anchoring element 2538. The dowel tip 2574 terminates with the antero-laterally facing planar surface 2572, the antero-medially facing planar surface 2578, and the postero-laterally facing planar surface 2578. The interaction of the dowel tip 2574 and the bone tunnel mouth may cause the anchoring element 2538 to bend toward the anchoring element 2540 as the dowel tip 2574 is inserted in the bone tunnel.

A slot 2564, or groove or channel, may be present along the dowel, the exposed side 2553 of the reinforcement plate 2552, or both. In cemented applications of the technology, the bone cement may flow along the slot(s) 2564 on the anchoring element.

The glenoid component 2500 may be operatively implanted in a scapula 2 (not shown). The scapula 2 includes a glenoid fossa 4, a coracoid process 6, and an acromion process 8. The triangular shape of the anchoring elements 2538, 2540 matches the conical shape of the glenoid vault more closely than does a central peg or keel, in a superior-inferior view. The dowels 2548 are peripherally arranged along the anterior portion 2522 in the example shown. This places the pedestal 2556 of the anchoring elements into regions of denser subchondral bone for stronger fixation. Medially in the glenoid vault, the side of the dowel 2548 and the exposed side 2553 of the reinforcement plate 2552 may lie adjacent and parallel to the thick cortical walls of the glenoid vault.

Figure 5A:
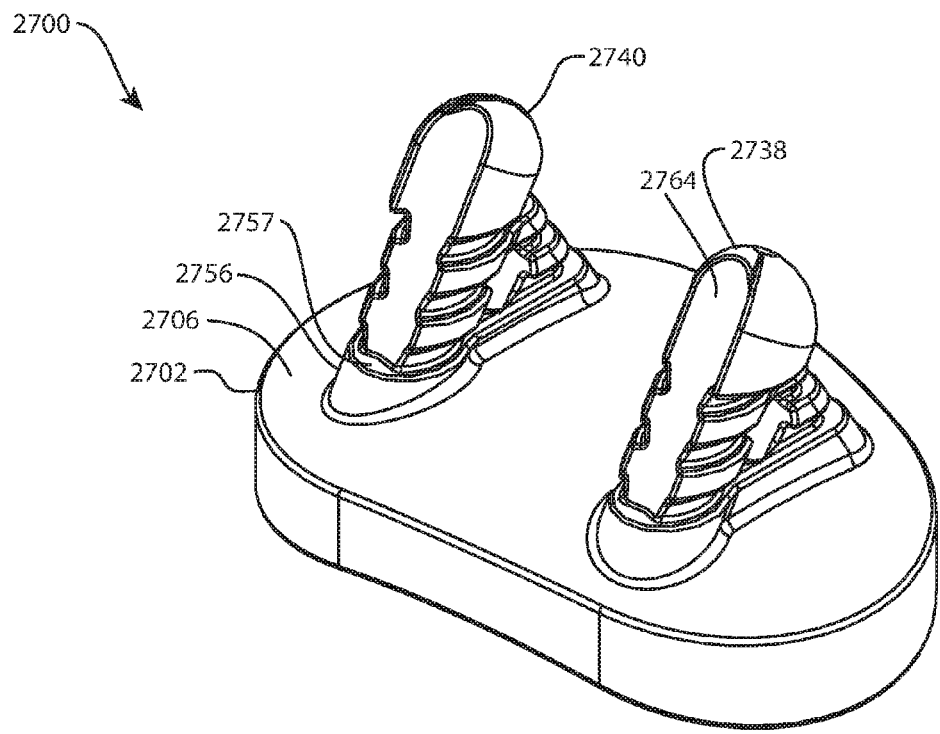
FIG. 5A is an isometric view of yet another left glenoid component.
Figure 5B:
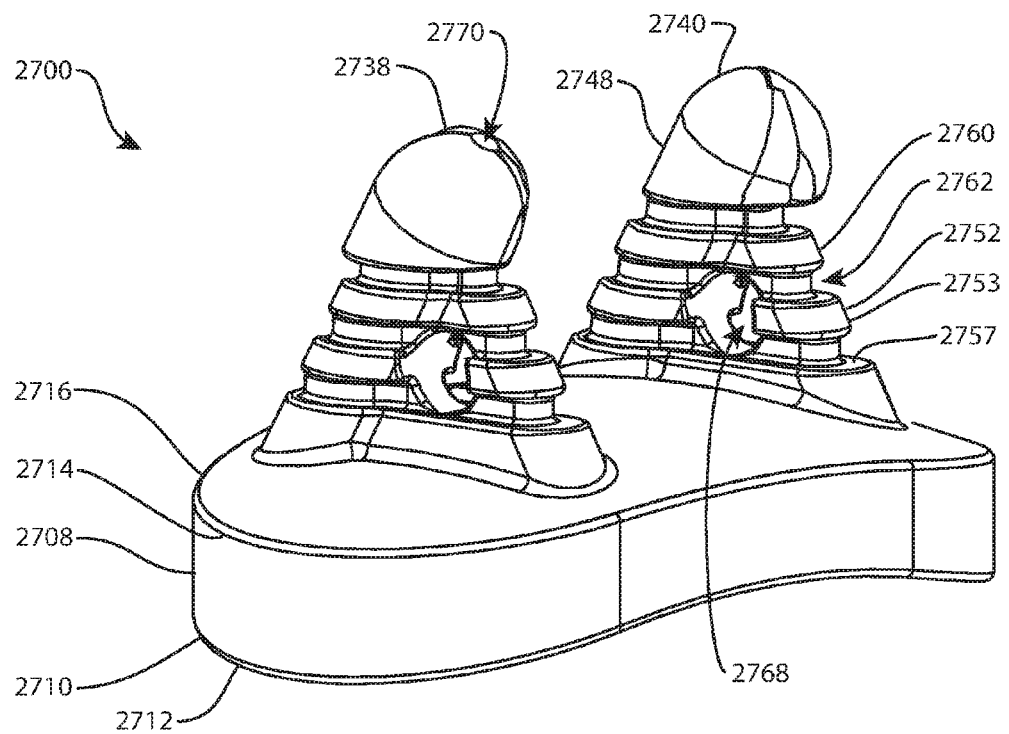
FIG. 5B is an oblique view of the glenoid component of FIG. 5A.
Figure 5C:
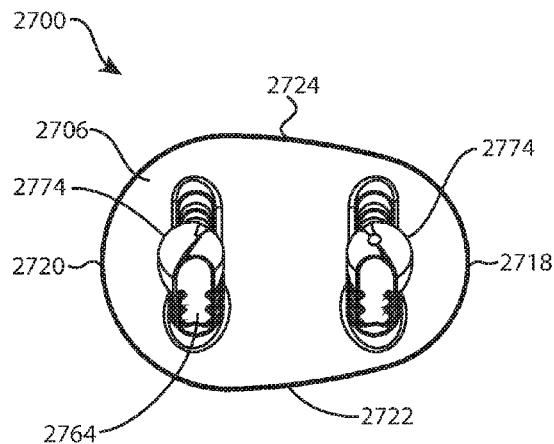
FIG. 5C is a medial view of the glenoid component of FIG. 5A.
Figure 5E:
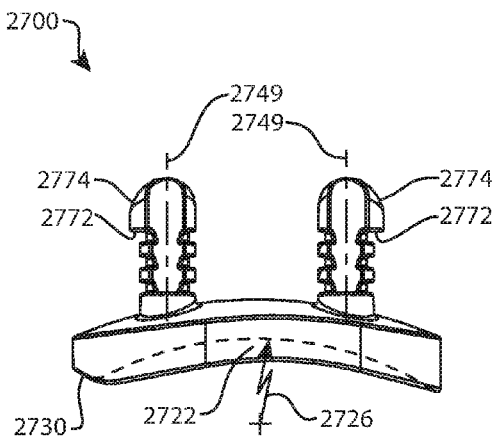
FIG. 5E is an anterior view of the glenoid component of FIG. 5A.
Figure 5D:
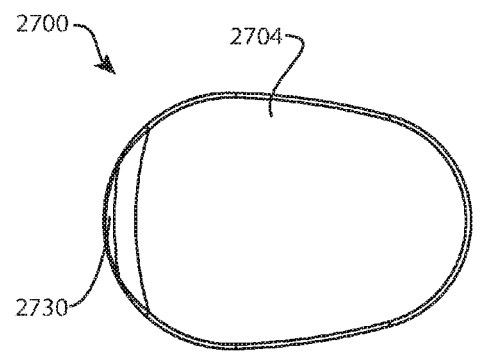
FIG. 5D is a lateral view of the glenoid component of FIG. 5A.
Figure 5F:
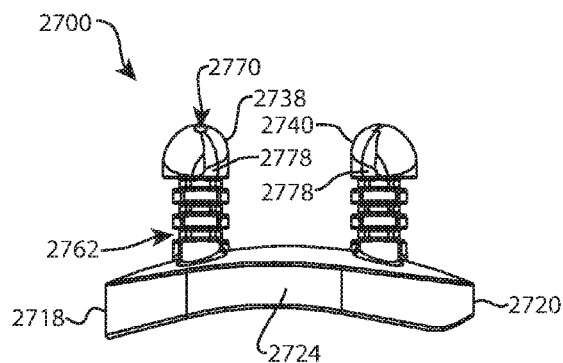
FIG. 5F is a posterior view of the glenoid component of FIG. 5A.
Figure 5G:
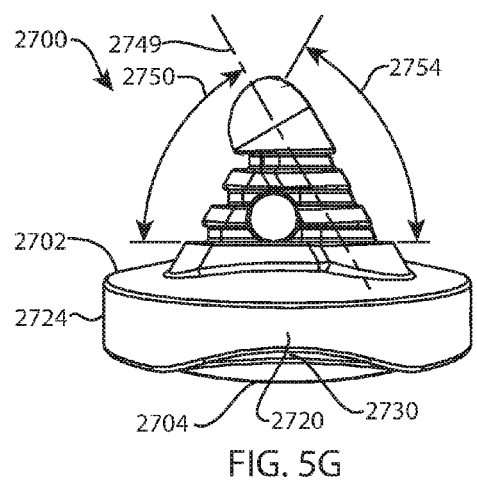
FIG. 5G is an inferior view of the glenoid component of FIG. 5A.
Figure 5H:
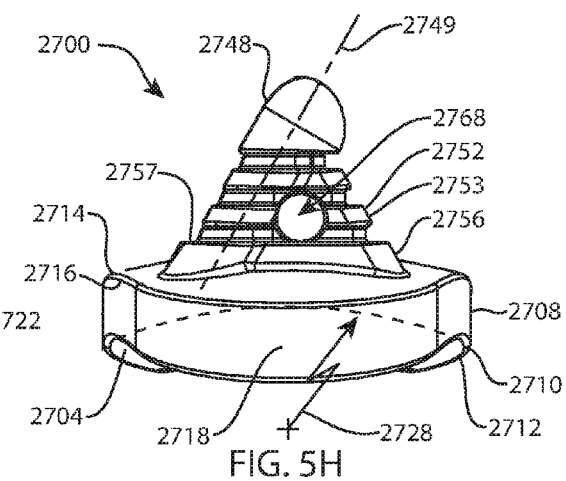
FIG. 5H is a superior view of the glenoid component of FIG. 5A.

Referring to FIGS. 5A-5H, a glenoid component 2700 includes a body 2702 with a lateral articular surface 2704 and an opposite medial bone-facing surface 2706.

A peripheral wall 2708 extends around the body 2702 between the surfaces 2704, 2706. A lateral peripheral edge 2710 extends around the body 2702 where the lateral articular surface 2704 intersects the peripheral wall 2708. The lateral peripheral edge 2710 may be rounded or relieved by a lateral peripheral relief 2712, such as a radius, fillet, chamfer, bevel, or the like. A medial peripheral edge 2714 extends around the body 2702 where the medial bone-facing surface 2706 intersects the peripheral wall 2708. The medial peripheral edge 2714 may be rounded or relieved by a medial peripheral relief 2716, such as a radius, fillet, chamfer, bevel, or the like.

The body 2702, lateral articular surface 2704, medial bone-facing surface 2706, peripheral wall 2708, lateral peripheral edge 2710, lateral peripheral relief 2712, medial peripheral edge 2714, and/or medial peripheral relief 2716 may be divided into a superior portion 2718, an inferior portion 2720, an anterior portion 2722, and a posterior portion 2724. The body 2702, lateral articular surface 2704, and/or medial bone-facing surface 2706 may also be divided into a peripheral portion near the peripheral wall 2708 and an interior or central portion. In examples other than shoulder glenoid components, where the surgical approach trajectory may be different than the approach described herein, the appropriate medical directional terms may be readily substituted by one of skill in the art.

The lateral articular surface 2704 may be concave as shown, planar, or convex in order to complement a natural or prosthetic humeral articular surface. The lateral articular surface 2704 may be spherical. The lateral articular surface 2704 may be elliptical or ovoid. The lateral articular surface 2704 may have a first radius 2726 which is dimensionally different from, i.e., larger or smaller than, a second radius 2728. The first radius 2726 may be a superior-inferior radius, or S-I radius. The second radius 2728 may be an anterior-posterior radius, or A-P radius.

The inferior portion 2720 of the body 2702 may include an inferior chamfer 2730 which extends between the lateral articular surface 2704 and the peripheral wall 2708. The inferior chamfer 2730 is a sloping surface, preferably a planar surface, that lowers the profile and thickness of the inferior portion 2720 along the lateral peripheral edge 2710.

The medial bone-facing surface 2706 may be convex as shown, planar, or concave.

The glenoid component 2700 includes at least one anchoring element 2738 which protrudes outwardly from the medial bone-facing surface 2706. The example shown includes a superior anchoring element 2738 and an inferior anchoring element 2740, although any number of anchoring elements may be present. Each anchoring element may be independently positioned on the medial bone-facing surface 2706, and may be independently sized.

Each anchoring element 2738, 2740 includes a dowel 2748, or mast, and a triangular reinforcement plate 2752, or sail or buttress.

The dowel 2748 projects from the medial bone-facing surface 2706 at an angle 2750 less than ninety degrees and greater than zero degrees. The angle 2750 may be referred to as a dowel angle or a mast angle. The angle 2750 may be measured between a central longitudinal axis 2749 of the dowel 2748 and a plane which is coplanar with the medial bone-facing surface 2706, if surface 2706 is planar, or a plane which is tangent to the medial bone-facing surface 2706, if surface 2706 is concave or convex. The plane may be tangent to the medial bone-facing surface 2706 at an intersection point between the central longitudinal axis 2749 of the dowel 2748 and the medial bone-facing surface 2706, or at a centroid of the medial bone-facing surface 2706. The dowel 2748 may project from the anterior portion 2722 of the body 2702, as shown, or from another portion of the body 2702. In the example shown, the dowels 2748 of anchoring elements 2738, 2740 project from peripheral locations in the anterior portion 2722 and terminate in medially located free ends. The dowel 2748 may have a round fundamental cross sectional shape, as shown, or another shape, such as a rectangle or dovetail. The dowel 2748 may include a hole 2770, which may receive a radiographic marker.

The reinforcement plate 2752 projects from the medial bone-facing surface 2706 in the acute angle 2750 between the dowel 2748 and the medial bone-facing surface 2706, and coplanar with the dowel 2748. An exposed side 2753 of the reinforcement plate 2752 projects from the medial bone-facing surface 2706 at an angle 2754 less than ninety degrees and greater than zero degrees. The angle 2754 may be referred to as a reinforcement angle. The angle 2754 opens toward the angle 2750, and the sum of angles 2750 and 2754 is greater than zero degrees and less than one hundred eighty degrees. The reinforcement plate 2752 intersects the dowel 2748 to form a triangular shape with one side formed by the medial bone-facing surface 2706, one side formed by the dowel 2748, and one side formed by the exposed side 2753 of the reinforcement plate 2752. The triangular shape may be an acute triangle having three internal angles each less than 90 degrees.

The anchoring elements 2738, 2740 may include a pedestal 2756 or footing where the anchoring element intersects the medial bone-facing surface 2706. The pedestal 2756 may be present on the dowel 2748 or the reinforcement plate 2752, or both. The pedestal 2756 may enlarge the anchoring element 2738, 2740 at the medial bone-facing surface 2706. The pedestal 2756 may terminate medially in a planar face 2757 which may establish the plane from which the angles 2750, 2754 are measured. The planar face 2757 may be tangent to the medial bone-facing surface 2706.

The anchoring elements 2738, 2740, including the dowels 2748, the reinforcement plates 2752, and the pedestals 2756, may project outwardly from the medial bone-facing surface 2706 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 2738, and on the inferior side of the inferior anchoring element 2740, or vice versa.

The anchoring elements 2738, 2740 may include surface features to improve fixation, or pull-out strength, after implantation. Surface features may be present on one or more of the anchoring elements present on a glenoid component. The surface features may project outwardly or inwardly from the fundamental surface(s) of the anchoring elements 2738, 2740. The surface features may include notches, grooves, channels, ridges, accordion texture, barbs, threads, shelves, rings, ribs, or perforations. For example, alternating ridges 2760 and grooves 2762 are shown, as well as fenestrations 2768 extending through the anchoring elements 2738, 2740. The illustrated ridges 2760 and grooves 2762 are oriented to resist axial pull-out, i.e., forces acting perpendicular to the back side of the glenoid component, or the face 2757 described below. The illustrated fenestrations 2768 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 2738 or 2740. For example, the dowel 2748 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 2738, 2740 to bend when inserted into the bone tunnel.

The anchoring elements 2738, 2740 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 2738, 2740 may include one or more surface features that are resistant to axial pull-out, i.e., forces acting perpendicular to the back side of the glenoid component, or the face 2757. The anchoring elements 2738, 2740 are illustrated with surface features which are protruding planar surfaces 2772 which face laterally. The planar surfaces 2772 may protrude from the superior and/or inferior side of each dowel 2748 to increase the width of the dowel. One planar surface 2772 is shown protruding from the superior-posterior side of the dowel 2748 of the superior anchoring element 2738 and a second planar surface 2772 is shown protruding from the inferior-posterior side of the dowel 2748 of the inferior anchoring element 2740. The planar surfaces 2772 are parallel to the face 2757 of the pedestal 2756.

The anchoring elements 2738, 2740 may include one or more surface features that are resistant to pullout forces acting perpendicular to the central longitudinal axis 2749 of the dowel 2748. The anchoring elements 2738, 2740 are illustrated with surface features which are protruding planar surfaces 2778. The planar surfaces 2778 may protrude from the anterior and/or posterior side of each dowel 2748 to increase the width of the dowel. Two planar surfaces 2778 are shown, with one planar surface 2778 facing postero-lateral-inferior on the superior anchoring element 2738, and a second planar surface 2778 is shown facing postero-lateral-superior, on the inferior anchoring element 2740. The planar surfaces 2778 are parallel to the central longitudinal axis 2749 of the dowel 2748.

The anchoring elements 2738, 2740 may include one or more surface features that are resistant to side-to-side translation of the glenoid component 2700, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 2738 is illustrated with a translation resistant surface feature which is a protruding dowel tip 2774, which is enlarged relative to the fundamental surface of the dowel 2748. The dowel tip 2774 may protrude from the superior and/or inferior side of each dowel 2748 to increase the width of the dowel to resist translation. One dowel tip 2774 is shown protruding from the superior-posterior side of the dowel 2748 of the superior anchoring element 2738, and a second dowel tip 2774 is shown protruding from the inferior-posterior side of the dowel 2748 of the inferior anchoring element 2740. The dowel tip 2774 terminates with the antero-laterally facing planar surface 2772, and the postero-lateral-inferior facing planar surface 2778 or the postero-lateral-superior facing planar surface 2778. The interaction of the dowel tip 2774 and the bone tunnel mouth may cause the anchoring element 2738 to bend toward the anchoring element 2740 as the dowel tip 2774 is inserted in the bone tunnel.

A slot 2764, or groove or channel, may be present along the dowel, the exposed side 2753 of the reinforcement plate 2752, or both. In cemented applications of the technology, the bone cement may flow along the slot(s) 2764 on the anchoring element.

The glenoid component 2700 may be operatively implanted in a scapula 2 (not shown). The scapula 2 includes a glenoid fossa 4, a coracoid process 6, and an acromion process 8. The triangular shape of the anchoring elements 2738, 2740 matches the conical shape of the glenoid vault more closely than does a central peg or keel, in a superior-inferior view. The dowels 2748 are peripherally arranged along the anterior portion 2722 in the example shown. This places the pedestal 2756 of the anchoring elements into regions of denser subchondral bone for stronger fixation. Medially in the glenoid vault, the side of the dowel 2748 and the exposed side 2753 of the reinforcement plate 2752 may lie adjacent and parallel to the thick cortical walls of the glenoid vault.

Figure 6A:
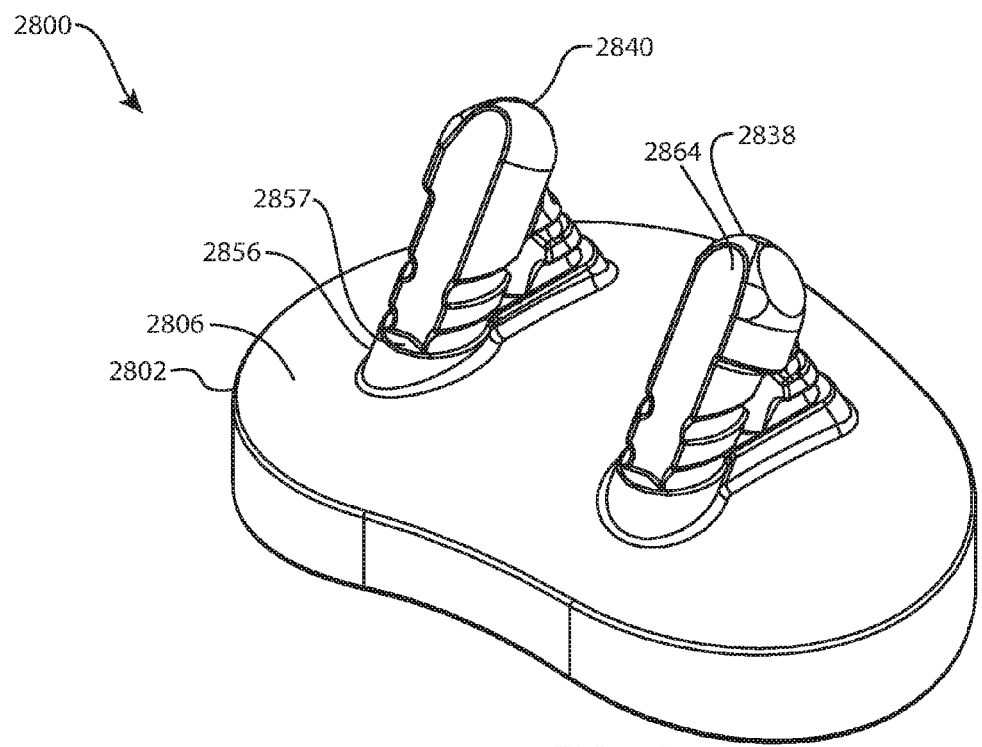
FIG. 6A is an isometric view of yet another left glenoid component.
Figure 6B:
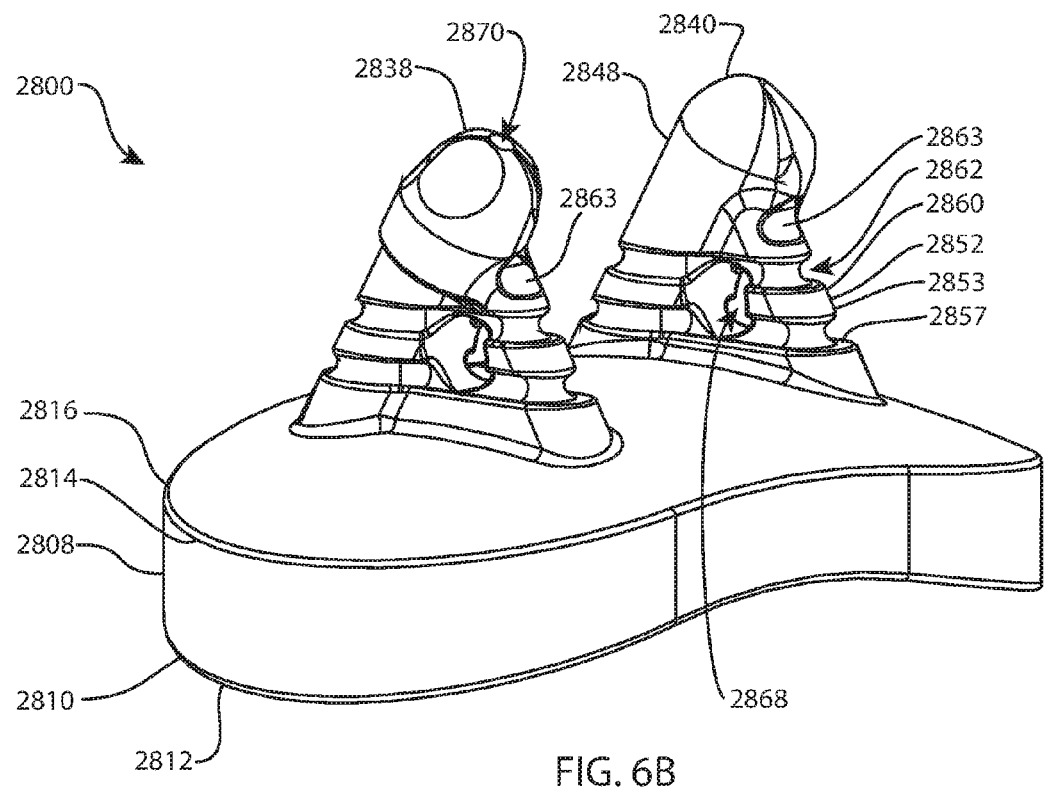
FIG. 6B is an oblique view of the glenoid component of FIG. 6A.
Figure 6C:
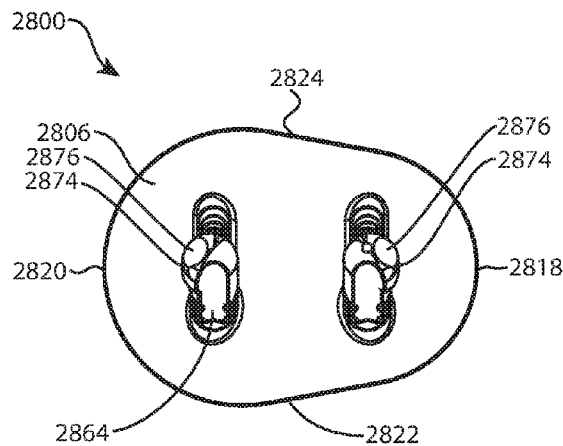
FIG. 6C is a medial view of the glenoid component of FIG. 6A.
Figure 6E:
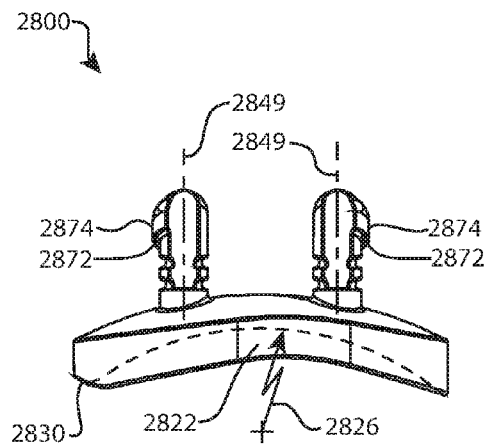
FIG. 6E is an anterior view of the glenoid component of FIG. 6A.
Figure 6D:
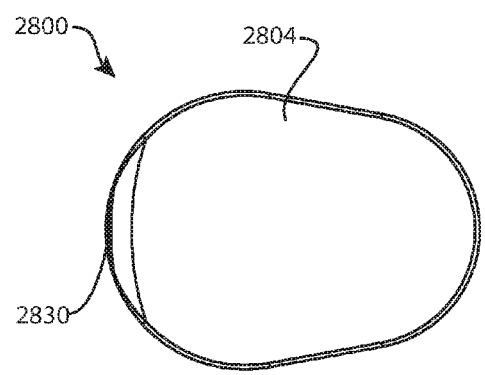
FIG. 6D is a lateral view of the glenoid component of FIG. 6A.
Figure 6F:
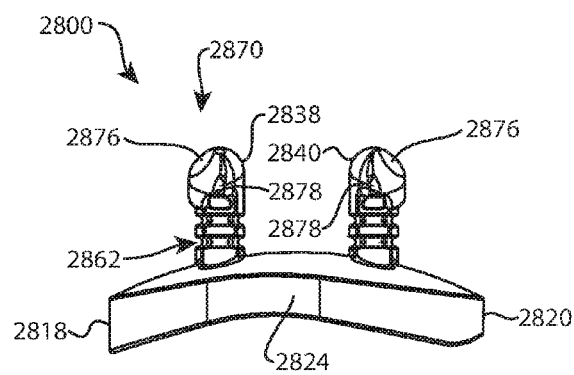
FIG. 6F is a posterior view of the glenoid component of FIG. 6A.
Figure 6G:
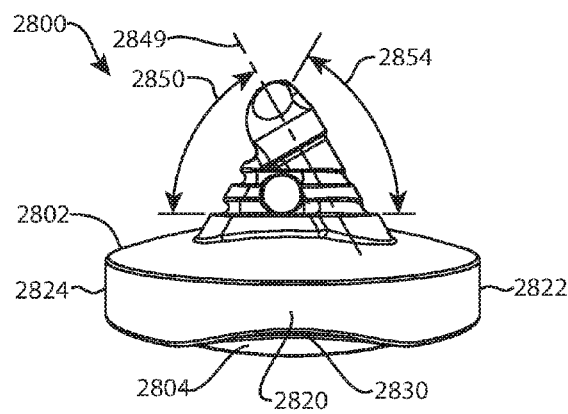
FIG. 6G is an inferior view of the glenoid component of FIG. 6A.
Figure 6H:
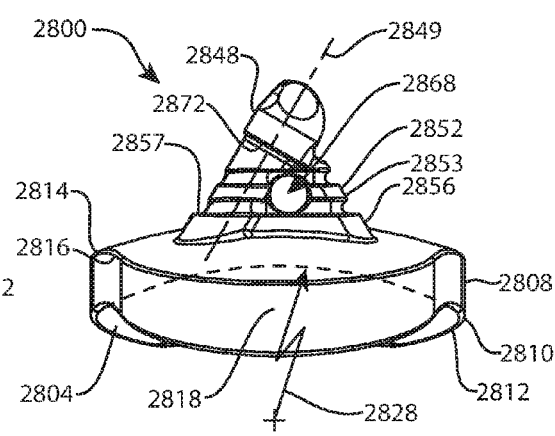
FIG. 6H is a superior view of the glenoid component of FIG. 6A.

Referring to FIGS. 6A-6H, a glenoid component 2800 includes a body 2802 with a lateral articular surface 2804 and an opposite medial bone-facing surface 2806.

A peripheral wall 2808 extends around the body 2802 between the surfaces 2804, 2806. A lateral peripheral edge 2810 extends around the body 2802 where the lateral articular surface 2804 intersects the peripheral wall 2808. The lateral peripheral edge 2810 may be rounded or relieved by a lateral peripheral relief 2812, such as a radius, fillet, chamfer, bevel, or the like. A medial peripheral edge 2814 extends around the body 2802 where the medial bone-facing surface 2806 intersects the peripheral wall 2808. The medial peripheral edge 2814 may be rounded or relieved by a medial peripheral relief 2816, such as a radius, fillet, chamfer, bevel, or the like.

The body 2802, lateral articular surface 2804, medial bone-facing surface 2806, peripheral wall 2808, lateral peripheral edge 2810, lateral peripheral relief 2812, medial peripheral edge 2814, and/or medial peripheral relief 2816 may be divided into a superior portion 2818, an inferior portion 2820, an anterior portion 2822, and a posterior portion 2824. The body 2802, lateral articular surface 2804, and/or medial bone-facing surface 2806 may also be divided into a peripheral portion near the peripheral wall 2808 and an interior or central portion. In examples other than shoulder glenoid components, where the surgical approach trajectory may be different than the approach described herein, the appropriate medical directional terms may be readily substituted by one of skill in the art.

The lateral articular surface 2804 may be concave as shown, planar, or convex in order to complement a natural or prosthetic humeral articular surface. The lateral articular surface 2804 may be spherical. The lateral articular surface 2804 may be elliptical or ovoid. The lateral articular surface 2804 may have a first radius 2826 which is dimensionally different from, i.e., larger or smaller than, a second radius 2828. The first radius 2826 may be a superior-inferior radius, or S-I radius. The second radius 2828 may be an anterior-posterior radius, or A-P radius.

The inferior portion 2820 of the body 2802 may include an inferior chamfer 2830 which extends between the lateral articular surface 2804 and the peripheral wall 2808. The inferior chamfer 2830 is a sloping surface, preferably a planar surface, that lowers the profile and thickness of the inferior portion 2820 along the lateral peripheral edge 2810.

The medial bone-facing surface 2806 may be convex as shown, planar, or concave.

The glenoid component 2800 includes at least one anchoring element 2838 which protrudes outwardly from the medial bone-facing surface 2806. The example shown includes a superior anchoring element 2838 and an inferior anchoring element 2840, although any number of anchoring elements may be present. Each anchoring element may be independently positioned on the medial bone-facing surface 2806, and may be independently sized.

Each anchoring element 2838, 2840 includes a dowel 2848, or mast, and a triangular reinforcement plate 2852, or sail or buttress.

The dowel 2848 projects from the medial bone-facing surface 2806 at an angle 2850 less than ninety degrees and greater than zero degrees. The angle 2850 may be referred to as a dowel angle or a mast angle. The angle 2850 may be measured between a central longitudinal axis 2849 of the dowel 2848 and a plane which is coplanar with the medial bone-facing surface 2806, if surface 2806 is planar, or a plane which is tangent to the medial bone-facing surface 2806, if surface 2806 is concave or convex. The plane may be tangent to the medial bone-facing surface 2806 at an intersection point between the central longitudinal axis 2849 of the dowel 2848 and the medial bone-facing surface 2806, or at a centroid of the medial bone-facing surface 2806. The dowel 2848 may project from the anterior portion 2822 of the body 2802, as shown, or from another portion of the body 2802. In the example shown, the dowels 2848 of anchoring elements 2838, 2840 project from peripheral locations in the anterior portion 2822 and terminate in medially located free ends. The dowel 2848 may have a round fundamental cross sectional shape, as shown, or another shape, such as a rectangle or dovetail. The dowel 2848 may include a hole 2870, which may receive a radiographic marker.

The reinforcement plate 2852 projects from the medial bone-facing surface 2806 in the acute angle 2850 between the dowel 2848 and the medial bone-facing surface 2806, and coplanar with the dowel 2848. An exposed side 2853 of the reinforcement plate 2852 projects from the medial bone-facing surface 2806 at an angle 2854 less than ninety degrees and greater than zero degrees. The angle 2854 may be referred to as a reinforcement angle. The angle 2854 opens toward the angle 2850, and the sum of angles 2850 and 2854 is greater than zero degrees and less than one hundred eighty degrees. The reinforcement plate 2852 intersects the dowel 2848 to form a triangular shape with one side formed by the medial bone-facing surface 2806, one side formed by the dowel 2848, and one side formed by the exposed side 2853 of the reinforcement plate 2852. The triangular shape may be an acute triangle having three internal angles each less than 90 degrees.

The anchoring elements 2838, 2840 may include a pedestal 2856 or footing where the anchoring element intersects the medial bone-facing surface 2806. The pedestal 2856 may be present on the dowel 2848 or the reinforcement plate 2852, or both. The pedestal 2856 may enlarge the anchoring element 2838, 2840 at the medial bone-facing surface 2806. The pedestal 2856 may terminate medially in a planar face 2857 which may establish the plane from which the angles 2850, 2854 are measured. The planar face 2857 may be tangent to the medial bone-facing surface 2806.

The anchoring elements 2838, 2840, including the dowels 2848, the reinforcement plates 2852, and the pedestals 2856, may project outwardly from the medial bone-facing surface 2806 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 2838, and on the inferior side of the inferior anchoring element 2840, or vice versa.

The anchoring elements 2838, 2840 may include surface features to improve fixation, or pull-out strength, after implantation. Surface features may be present on one or more of the anchoring elements present on a glenoid component. The surface features may project outwardly or inwardly from the fundamental surface(s) of the anchoring elements 2838, 2840. The surface features may include notches, grooves, channels, ridges, accordion texture, barbs, threads, shelves, rings, ribs, or perforations. For example, alternating ridges 2860 and grooves 2862 are shown, as well as fenestrations 2868 extending through the anchoring elements 2838, 2840. The illustrated ridges 2860 and grooves 2862 are oriented to resist axial pull-out, i.e., forces acting perpendicular to the back side of the glenoid component, or the face 2857 described below. The illustrated fenestrations 2868 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 2838 or 2840. For example, the dowel 2848 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 2838, 2840 to bend when inserted into the bone tunnel.

The anchoring elements 2838, 2840 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 2838, 2840 may include one or more surface features that are resistant to pullout forces acting along the central longitudinal axis 2849 of the dowel 2848. The anchoring elements 2838, 2840 are illustrated with surface features which are protruding planar surfaces 2872 which face antero-laterally. The planar surfaces 2872 may protrude from the superior and/or inferior sides of each dowel 2848 to increase the width of the dowel. Two planar surfaces 2872 are shown, with a first planar surface 2872 protruding from the superior-posterior side of the dowel 2848 of the superior anchoring element 2838, and a second planar surface 2872 protruding from the inferior-posterior side of the dowel 2848 of the inferior anchoring element 2840. The planar surfaces 2872 are perpendicular to the central longitudinal axis 2849 of the dowel 2848.

The anchoring elements 2838, 2840 may include one or more surface features that are resistant to pullout forces acting perpendicular to the central longitudinal axis 2849 of the dowel 2848. The anchoring elements 2838, 2840 are illustrated with surface features which are protruding planar surfaces 2878. The planar surfaces 2878 may protrude from the anterior and/or posterior side of each dowel 2848 to increase the width of the dowel. Two planar surfaces 2878 are shown, with one planar surface 2878 facing postero-lateral-inferior on the superior anchoring element 2838, and a second planar surface 2878 is shown facing postero-lateral-superior, on the inferior anchoring element 2840. The planar surfaces 2878 are parallel to the central longitudinal axis 2849 of the dowel 2848.

The anchoring elements 2838, 2840 may include one or more surface features that are resistant to side-to-side translation of the glenoid component 2800, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature.

The anchoring elements 2838, 2840 may include one or more surface features that are resistant to side-to-side translation of the glenoid component 2800, i.e., translation in the superior-inferior and/or anterior-posterior directions. The anchoring elements 2838, 2840 are illustrated with translation resistant surface features which are protruding dowel tips 2874, which are enlarged relative to the fundamental surface of the dowel 2848. The dowel tips 2874 may protrude from the superior and/or inferior sides of each dowel 2848 to increase the width of the dowel to resist translation. Two dowel tips 2874 are shown, with a first dowel tip 2874 protruding from the superior-posterior side of the dowel 2848 of the superior anchoring element 2838, and a second dowel tip 2874 protruding from the inferior-posterior side of the dowel 2848 of the inferior anchoring element 2840. The dowel tips 2874 terminate with the antero-laterally facing planar surfaces 2872. A beveled surface 2876 may be present near the medial free end of the dowel tip 2874. Two beveled surfaces 2876 are shown, with a first beveled surface 2876 facing superior-posterior on the superior anchoring element 2838, and a second beveled surface 2876 facing inferior-posterior on the inferior anchoring element 2840. The beveled surface(s) 2876 may reduce the force required to initially insert the dowel tips 2874 in the corresponding bone tunnels, and the interaction of the beveled surfaces 2876 and the bone tunnel mouths may cause the anchoring elements 2838, 2840 to bend toward each other as the dowel tips 2874 are inserted in the bone tunnels.

A slot 2864, or groove or channel, may be present along the dowel, the exposed side 2853 of the reinforcement plate 2852, or both. In cemented applications of the technology, the bone cement may flow along the slot(s) 2864 on the anchoring element.

The glenoid component 2800 may be operatively implanted in a scapula 2 (not shown). The scapula 2 includes a glenoid fossa 4, a coracoid process 6, and an acromion process 8. The triangular shape of the anchoring elements 2838, 2840 matches the conical shape of the glenoid vault more closely than does a central peg or keel, in a superior-inferior view. The dowels 2848 are peripherally arranged along the anterior portion 2822 in the example shown. This places the pedestal 2856 of the anchoring elements into regions of denser subchondral bone for stronger fixation. Medially in the glenoid vault, the side of the dowel 2848 and the exposed side 2853 of the reinforcement plate 2852 may lie adjacent and parallel to the thick cortical walls of the glenoid vault.

A notch 2863 may be present on the exposed side 2853 of the reinforcement plate 2852 adjacent to the dowel 2848. The notch 2863 provides relief in the anchoring elements 2838, 2840 to avoid impingement with the bone tunnel (or socket).

Figure 7A:
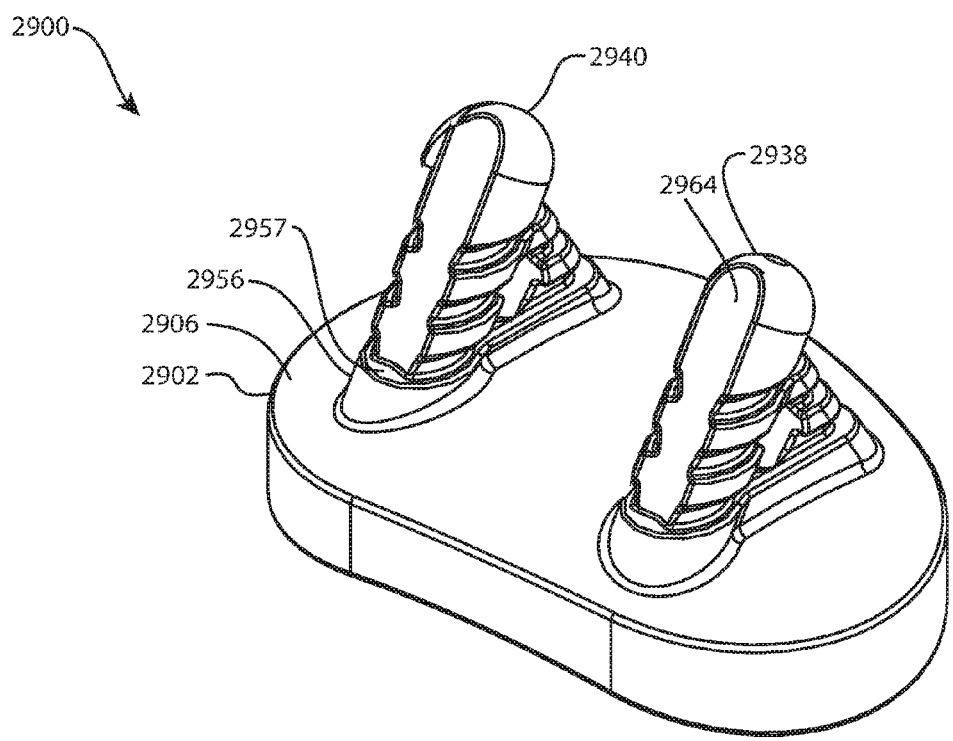
FIG. 7A is an isometric view of yet another left glenoid component.
Figure 7B:
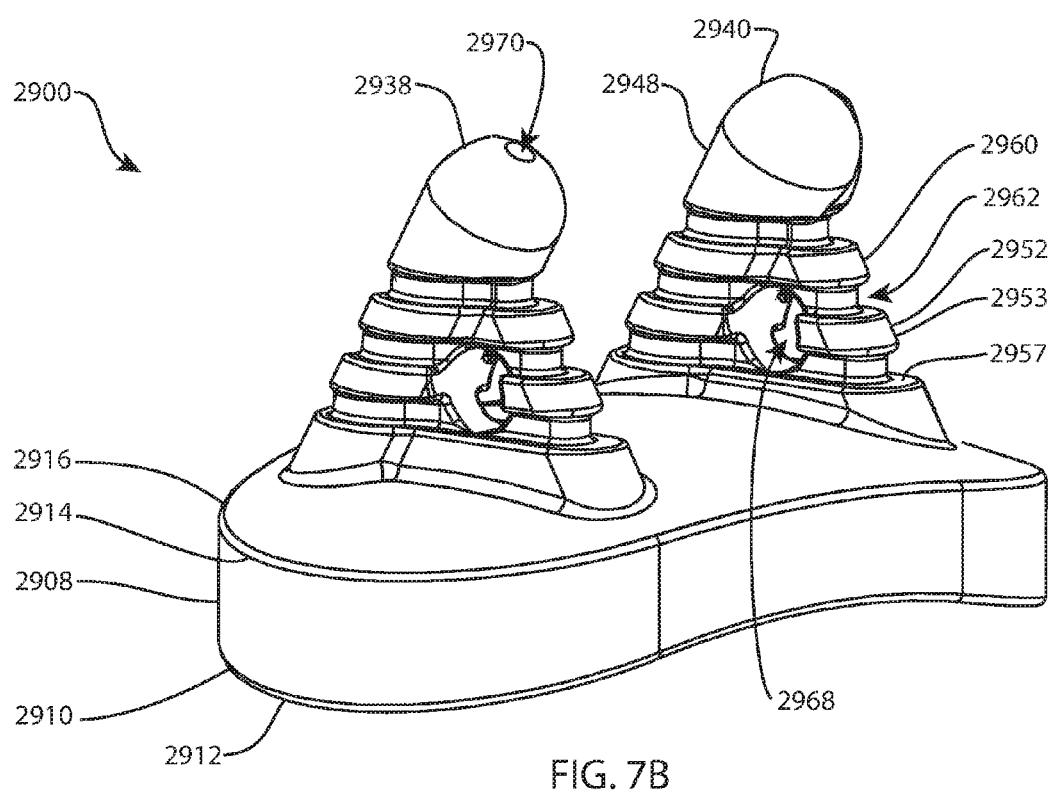
FIG. 7B is an oblique view of the glenoid component of FIG. 7A.
Figure 7C:
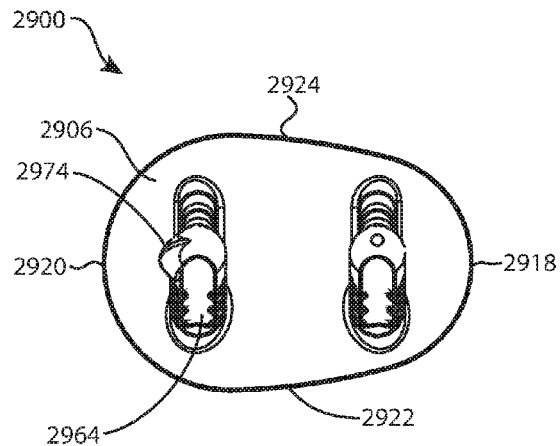
FIG. 7C is a medial view of the glenoid component of FIG. 7A.
Figure 7E:
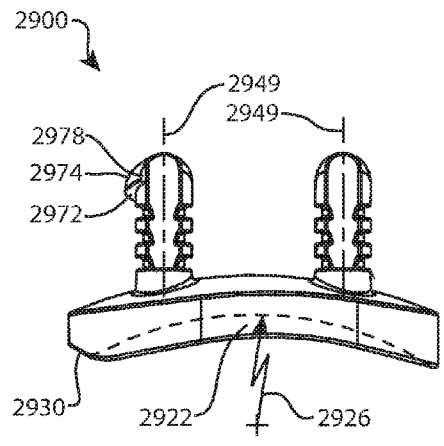
FIG. 7E is an anterior view of the glenoid component of FIG. 7A.
Figure 7D:
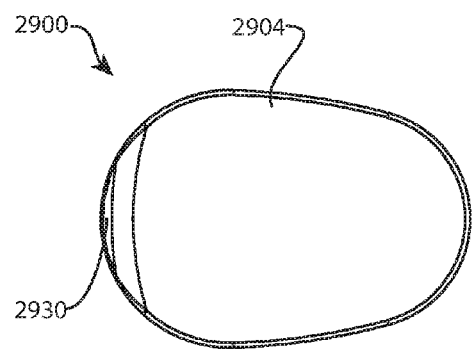
FIG. 7D is a lateral view of the glenoid component of FIG. 7A.
Figure 7F:
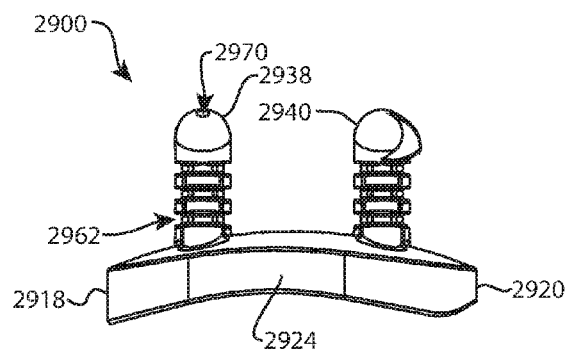
FIG. 7F is a posterior view of the glenoid component of FIG. 7A.
Figure 7G:
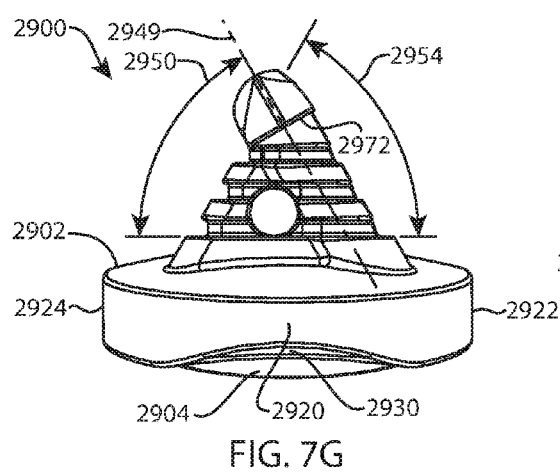
FIG. 7G is an inferior view of the glenoid component of FIG. 7A.
Figure 7H:
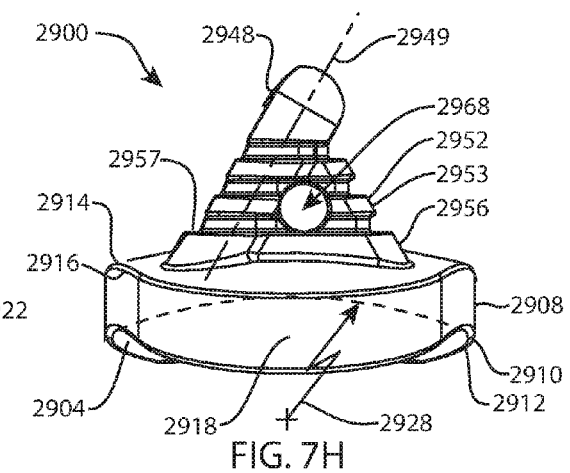
FIG. 7H is a superior view of the glenoid component of FIG. 7A.

Referring to FIGS. 7A-7H, a glenoid component 2900 includes a body 2902 with a lateral articular surface 2904 and an opposite medial bone-facing surface 2906.

A peripheral wall 2908 extends around the body 2902 between the surfaces 2904, 2906. A lateral peripheral edge 2910 extends around the body 2902 where the lateral articular surface 2904 intersects the peripheral wall 2908. The lateral peripheral edge 2910 may be rounded or relieved by a lateral peripheral relief 2912, such as a radius, fillet, chamfer, bevel, or the like. A medial peripheral edge 2914 extends around the body 2902 where the medial bone-facing surface 2906 intersects the peripheral wall 2908. The medial peripheral edge 2914 may be rounded or relieved by a medial peripheral relief 2916, such as a radius, fillet, chamfer, bevel, or the like.

The body 2902, lateral articular surface 2904, medial bone-facing surface 2906, peripheral wall 2908, lateral peripheral edge 2910, lateral peripheral relief 2912, medial peripheral edge 2914, and/or medial peripheral relief 2916 may be divided into a superior portion 2918, an inferior portion 2920, an anterior portion 2922, and a posterior portion 2924. The body 2902, lateral articular surface 2904, and/or medial bone-facing surface 2906 may also be divided into a peripheral portion near the peripheral wall 2908 and an interior or central portion. In examples other than shoulder glenoid components, where the surgical approach trajectory may be different than the approach described herein, the appropriate medical directional terms may be readily substituted by one of skill in the art.

The lateral articular surface 2904 may be concave as shown, planar, or convex in order to complement a natural or prosthetic humeral articular surface. The lateral articular surface 2904 may be spherical. The lateral articular surface 2904 may be elliptical or ovoid. The lateral articular surface 2904 may have a first radius 2926 which is dimensionally different from, i.e., larger or smaller than, a second radius 2928. The first radius 2926 may be a superior-inferior radius, or S-I radius. The second radius 2928 may be an anterior-posterior radius, or A-P radius.

The inferior portion 2920 of the body 2902 may include an inferior chamfer 2930 which extends between the lateral articular surface 2904 and the peripheral wall 2908. The inferior chamfer 2930 is a sloping surface, preferably a planar surface, that lowers the profile and thickness of the inferior portion 2920 along the lateral peripheral edge 2910.

The medial bone-facing surface 2906 may be convex as shown, planar, or concave.

The glenoid component 2900 includes at least one anchoring element 2938 which protrudes outwardly from the medial bone-facing surface 2906. The example shown includes a superior anchoring element 2938 and an inferior anchoring element 2940, although any number of anchoring elements may be present. Each anchoring element may be independently positioned on the medial bone-facing surface 2906, and may be independently sized.

Each anchoring element 2938, 2940 includes a dowel 2948, or mast, and a triangular reinforcement plate 2952, or sail or buttress.

The dowel 2948 projects from the medial bone-facing surface 2906 at an angle 2950 less than ninety degrees and greater than zero degrees. The angle 2950 may be referred to as a dowel angle or a mast angle. The angle 2950 may be measured between a central longitudinal axis 2949 of the dowel 2948 and a plane which is coplanar with the medial bone-facing surface 2906, if surface 2906 is planar, or a plane which is tangent to the medial bone-facing surface 2906, if surface 2906 is concave or convex. The plane may be tangent to the medial bone-facing surface 2906 at an intersection point between the central longitudinal axis 2949 of the dowel 2948 and the medial bone-facing surface 2906, or at a centroid of the medial bone-facing surface 2906. The dowel 2948 may project from the anterior portion 2922 of the body 2902, as shown, or from another portion of the body 2902. In the example shown, the dowels 2948 of anchoring elements 2938, 2940 project from peripheral locations in the anterior portion 2922 and terminate in medially located free ends. The dowel 2948 may have a round fundamental cross sectional shape, as shown, or another shape, such as a rectangle or dovetail. The dowel 2948 may include a hole 2970, which may receive a radiographic marker.

The reinforcement plate 2952 projects from the medial bone-facing surface 2906 in the acute angle 2950 between the dowel 2948 and the medial bone-facing surface 2906, and coplanar with the dowel 2948. An exposed side 2953 of the reinforcement plate 2952 projects from the medial bone-facing surface 2906 at an angle 2954 less than ninety degrees and greater than zero degrees. The angle 2954 may be referred to as a reinforcement angle. The angle 2954 opens toward the angle 2950, and the sum of angles 2950 and 2954 is greater than zero degrees and less than one hundred eighty degrees. The reinforcement plate 2952 intersects the dowel 2948 to form a triangular shape with one side formed by the medial bone-facing surface 2906, one side formed by the dowel 2948, and one side formed by the exposed side 2953 of the reinforcement plate 2952. The triangular shape may be an acute triangle having three internal angles each less than 90 degrees.

The anchoring elements 2938, 2940 may include a pedestal 2956 or footing where the anchoring element intersects the medial bone-facing surface 2906. The pedestal 2956 may be present on the dowel 2948 or the reinforcement plate 2952, or both. The pedestal 2956 may enlarge the anchoring element 2938, 2940 at the medial bone-facing surface 2906. The pedestal 2956 may terminate medially in a planar face 2957 which may establish the plane from which the angles 2950, 2954 are measured. The planar face 2957 may be tangent to the medial bone-facing surface 2906.

The anchoring elements 2938, 2940, including the dowels 2948, the reinforcement plates 2952, and the pedestals 2956, may project outwardly from the medial bone-facing surface 2906 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 2938, and on the inferior side of the inferior anchoring element 2940, or vice versa.

The anchoring elements 2938, 2940 may include surface features to improve fixation, or pull-out strength, after implantation. Surface features may be present on one or more of the anchoring elements present on a glenoid component. The surface features may project outwardly or inwardly from the fundamental surface(s) of the anchoring elements 2938, 2940. The surface features may include notches, grooves, channels, ridges, accordion texture, barbs, threads, shelves, rings, ribs, or perforations. For example, alternating ridges 2960 and grooves 2962 are shown, as well as fenestrations 2968 extending through the anchoring elements 2938, 2940. The illustrated ridges 2960 and grooves 2962 are oriented to resist axial pull-out, i.e., forces acting perpendicular to the back side of the glenoid component, or the face 2957 described below. The illustrated fenestrations 2968 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 2938 or 2940. For example, the dowel 2948 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 2938, 2940 to bend when inserted into the bone tunnel.

The anchoring elements 2938, 2940 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 2938, 2940 may include one or more surface features that are resistant to pullout forces acting along the central longitudinal axis 2949 of the dowel 2948. The anchoring element 2940 is illustrated with a surface feature which is a protruding planar surface 2972 which faces antero-laterally. The planar surface 2972 may protrude from the superior and/or inferior sides of each dowel 2948 to increase the width of the dowel. A planar surface 2972 is shown protruding from the inferior side of the dowel 2948 of the inferior anchoring element 2940. The planar surface 2972 is perpendicular to the central longitudinal axis 2949 of the dowel 2948.

The anchoring elements 2938, 2940 may include one or more surface features that are resistant to pullout forces acting perpendicular to the central longitudinal axis 2949 of the dowel 2948. The anchoring element 2940 is illustrated with a surface feature which is a protruding planar surface 2978. The planar surface 2978 may protrude from the anterior and/or posterior side of each dowel 2948 to increase the width of the dowel. A planar surface 2978 is shown facing antero-medial on the inferior anchoring element 2940. The planar surface 2978 is parallel to the central longitudinal axis 2949 of the dowel 2948.

The anchoring elements 2938, 2940 may include one or more surface features that are resistant to side-to-side translation of the glenoid component 2900, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 2940 is illustrated with a translation resistant surface feature which is protruding dowel tip 2974, which is enlarged relative to the fundamental surface of the dowel 2948. The dowel tip 2974 may protrude from the superior and/or inferior sides of each dowel 2948 to increase the width of the dowel to resist translation. A dowel tip 2974 is shown protruding from the inferior side of the dowel 2948 of the inferior anchoring element 2940. The dowel tip 2974 terminates with the antero-laterally facing planar surface 2972.

A slot 2964, or groove or channel, may be present along the dowel, the exposed side 2953 of the reinforcement plate 2952, or both. In cemented applications of the technology, the bone cement may flow along the slot(s) 2964 on the anchoring element.

The glenoid component 2900 may be operatively implanted in a scapula 2 (not shown). The scapula 2 includes a glenoid fossa 4, a coracoid process 6, and an acromion process 8. The triangular shape of the anchoring elements 2938, 2940 matches the conical shape of the glenoid vault more closely than does a central peg or keel, in a superior-inferior view. The dowels 2948 are peripherally arranged along the anterior portion 2922 in the example shown. This places the pedestal 2956 of the anchoring elements into regions of denser subchondral bone for stronger fixation. Medially in the glenoid vault, the side of the dowel 2948 and the exposed side 2953 of the reinforcement plate 2952 may lie adjacent and parallel to the thick cortical walls of the glenoid vault.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. §112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. An arthroplasty system comprising:
a first arthroplasty prosthesis comprising a body and an anchoring element protruding from the body;
wherein the body comprises an articular surface and a bone-facing surface opposite the articular surface;
wherein the anchoring element comprises a reinforcement plate, a dowel, a first surface feature, and a second surface feature, wherein the first surface feature is resistant to forces acting along a first direction, wherein the second surface feature is resistant to forces acting along a second direction, wherein the first and second directions intersect or are skew;
wherein the reinforcement plate protrudes from the bone-facing surface, wherein the reinforcement plate has three sides that form an acute triangle;
wherein the dowel protrudes from the bone-facing surface at an acute first angle and extends along a first side of the reinforcement plate, wherein the dowel has a central longitudinal axis.

2. The system of claim 1, wherein the dowel comprises the first surface feature and the second surface feature, wherein the first direction is perpendicular to the bone-facing surface, wherein the second direction is parallel to the central longitudinal axis of the dowel.

3. The system of claim 2, wherein the first surface feature is a ridge extending across the dowel parallel to the bone-facing surface, wherein the second surface feature is a protruding planar surface extending across the dowel perpendicular to the central longitudinal axis of the dowel.

* * * * *